United States Patent
Simoneau et al.

(10) Patent No.: US 6,806,265 B2
(45) Date of Patent: Oct. 19, 2004

(54) NON-NUCLEOSIDE REVERSE TRANSCRIPTASE INHIBITORS

(75) Inventors: Bruno Simoneau, Laval (CA); Serge Landry, Laval (CA); Eric Malenfant, Laval (CA); Julie Naud, Laval (CA); Jeffrey O'Meara, Laval (CA); Bounkham Thavonekham, Laval (CA); Christiane Yoakim, Laval (CA)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 10/430,116

(22) Filed: May 6, 2003

(65) Prior Publication Data

US 2004/0006071 A1 Jan. 8, 2004

Related U.S. Application Data

(60) Provisional application No. 60/380,886, filed on May 16, 2002.

(51) Int. Cl.⁷ .................... C07D 471/14; A61K 31/55; A61P 31/18
(52) U.S. Cl. .................. 514/211.04; 540/495
(58) Field of Search .................. 540/495; 514/211.04

(56) References Cited

U.S. PATENT DOCUMENTS

| | | | |
|---|---|---|---|
| 5,366,972 A | 11/1994 | Hargrave et al. | 514/220 |
| 5,705,499 A | 1/1998 | Cywin et al. | 514/220 |
| 6,420,359 B1 | 7/2002 | Simoneau | 514/220 |
| 2002/0028807 A1 | 3/2002 | Simoneau et al. | |

FOREIGN PATENT DOCUMENTS

| | | |
|---|---|---|
| WO | WO 01/96338 A1 | 12/2001 |
| WO | WO 02/076982 A2 | 10/2002 |
| WO | WO 03/011862 A1 | 2/2003 |

OTHER PUBLICATIONS

Hargrave, K. D., et al; "Novel Non–Nucleoside Inhibitors of HIV–1 Reverse Transcriptase. 1. Tricyclic Pyridobenzo- and Dipyridodiazepinones"; J. Med. Chem. 1991, 34, pp. 2231–2241.

Berge, S. M. et al; "Pharmaceutical Salts"; J. Pharm. Sci. 1977, 66(1), pp. 1–19.

Klunder, J. M. et al; "Novel Nonnucleoside Inhibitors of HIV–1 Reverse Transcriptase. 7. 8–Arylethyldipyridodiazepinones as Potent Broad–Spectrum Inhibitors of Wild–Type and Mutant Enzymes"; J. Med. Chem. 1998, 41, pp. 2960–2971.

Primary Examiner—Richard L. Raymond
Assistant Examiner—Hong Liu
(74) Attorney, Agent, or Firm—Robert P. Raymond; Alan R. Stempel; Mary-Ellen M. Devlin

(57) ABSTRACT

Compounds represented by formula I:

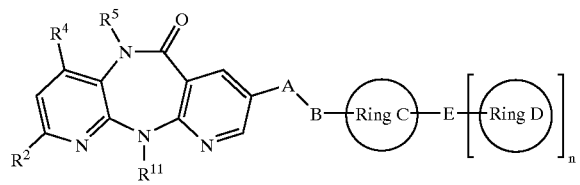

wherein
  $R^2$ is selected from the group consisting of H, $(C_{1-4})$alkyl, halo, haloalkyl, OH, $(C_{1-6})$alkoxy, $NH(C_{1-4}$alkyl) or $N(C_{1-4}$alkyl)$_2$; $R^4$ is H or Me; $R^5$ is H or Me; $R^{11}$ is H, $(C_{1-4})$alkyl, $(C_{3-4})$cycloalkyl and $(C_{1-4})$alkyl-$(C_{3-4})$ cycloalkyl; A is a connecting chain of $(C_{1-3})$alkyl; B is O or S; n is 0 or 1; wherein when n is 0:
  Ring C is 6- or 10-membered aryl or 5- or 6-membered heterocycle having from 1 to 4 heteroatoms selected from the group consisting of O, N, and S, said aryl and said heterocycle being optionally substituted;
  and E is $CONR^{12}R^{13}$; $CONHNR^{14}R^{15}$; $NR^{16}COR^{17}$; $NR^{18}SO_2(C_{1-6})$alkyl; $SO_2NR^{19}R^{20}$; or $SO_2R^{21}$; or
  when n is 1: Ring C is as defined above and E is a single bond or a connecting group; and
  Ring D is 6- or 10-membered aryl or 5- or 6-membered heterocycle having from 1 to 4 heteroatoms selected from the group consisting of O, N, and S, said aryl and said heterocycle being optionally substituted with from 1 to 5 substituents;
or a salt or a prodrug thereof are provided as inhibitors of HIV reverse transcriptase.

16 Claims, No Drawings

NON-NUCLEOSIDE REVERSE TRANSCRIPTASE INHIBITORS

RELATED APPLICATIONS

Benefit of U.S. Provisional Application, Ser. No. 60/380,886, filed on May 16, 2002, is hereby claimed.

TECHNICAL FIELD OF THE INVENTION

The invention relates to novel compounds and pharmaceutically acceptable salts thereof, their use, either alone or in combination with other therapeutic agents, in the treatment or prophylaxis of HIV infection, and to pharmaceutical compositions comprising these compounds.

BACKGROUND OF THE INVENTION

The disease known as acquired immune deficiency syndrome (AIDS) is caused by the human immunodeficiency virus (HIV), particularly the strain known as HIV-1. In order for HIV to be replicated by a host cell, the information of the viral genome must be integrated into the host cell's DNA. However, HIV is a retrovirus, meaning that its genetic information is in the form of RNA. The HIV replication cycle therefore requires a step of transcription of the viral genome (RNA) into DNA, which is the reverse of the normal chain of events. An enzyme that has been aptly dubbed reverse transcriptase (RT) accomplishes the transcription of the viral RNA into DNA. The HIV virion includes a copy of RT along with the viral RNA.

Reverse transcriptase has three known enzymatic functions; it acts as an RNA-dependent DNA polymerase, as a ribonuclease, and as a DNA-dependent DNA polymerase. Acting as an RNA-dependent DNA polymerase, RT transcribes a single-stranded DNA copy of the viral RNA. Acting as a ribonuclease, RT destroys the original viral RNA, and frees the DNA just produced from the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds that inhibit the enzymatic functions of HIV-1 reverse transcriptase will inhibit replication of HIV-1 in infected cells. Such compounds are useful in the prevention or treatment of HIV-1 infection in human subjects, as demonstrated by known RT inhibitors such as 3'-azido-3'-deoxythymidine (AZT), 2',3'-dideoxyinosine (ddI), 2',3'-dideoxycytidine (ddC), d4T, 3TC, Nevirapine, Delavirdine, Efavirenz and Abacavir, the main drugs thus far approved for use in the treatment of AIDS.

As with any antiviral therapy, use of RT inhibitors in the treatment of AIDS eventually leads to a virus that is less sensitive to the given drug. Resistance (reduced sensitivity) to these drugs is the result of mutations that occur in the reverse transcriptase segment of the pol gene. Several mutant strains of HIV have been characterized, and resistance to known therapeutic agents is due to mutations in the RT gene. Some of the most commonly observed mutants clinically are: the Y181C mutant, in which a tyrosine (Y), at codon 181, has been mutated to a cysteine (C) residue, and K103N where the lysine (K) at position 103 has been replaced by asparagine (N). Other mutants, which emerge with increasing frequency during treatment with known antivirals, include the single mutants V106A, G190A, Y188C, and P236L; and the double mutants K103N/Y181C, K103N/P225H, K103N/V108I, and K103N/L100I.

As therapy and prevention of HIV infection using antivirals continues, the emergence of new resistant strains is expected to increase. There is therefore an ongoing need for new inhibitors of RT, with different patterns of effectiveness against the various mutants.

Compounds having tricyclic structures, which are inhibitors of HIV-1, are described in U.S. Pat. No. 5,366,972. Other inhibitors of HIV-1 reverse transcriptase are described in Hargrave et al., J. Med Chem., 34, 2231 (1991).

U.S. Pat. No. 5,705,499 proposes 8-arylalkyl- and 8-arylheteroalkyl-5,11-dihydro-6H-dipyrido[3,2-B:2',3'-E][1,4]diazepines as inhibitors of RT.

WO 01/96338 and U.S. Pat. No. 6,420,359 disclose diazepine structures having quinoline and quinoline-N-oxide substituents as inhibitors of RT. The exemplified compounds have activity against HIV WT, single and double mutant strains. WO 02/076982 and WO 03/011862 also disclose diazepine structures having substituents structurally different from the present invention.

SUMMARY OF THE INVENTION

The present invention provides novel compounds that are potent inhibitors of wild type and double mutant strains of HIV-1 RT. Advantageously, the compounds of the present invention are effective at inhibiting the clinically significant double mutant K103N/Y181C.

In a first aspect of the invention, there is provided a compound represented by formula I:

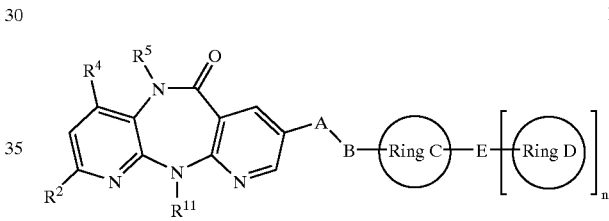

wherein
$R^2$ is selected from the group consisting of H, $(C_{1-4})$alkyl, halo, haloalkyl, OH, $(C_{1-6})$alkoxy, NH($C_{1-4}$alkyl) or N($C_{1-4}$alkyl)$_2$;
$R^4$ is H or Me;
$R^5$ is H or Me;
$R^{11}$ is H, $(C_{1-4})$alkyl, $(C_{3-4})$cycloalkyl and $(C_{1-4})$alkyl-$(C_{3-4})$cycloalkyl;
A is a connecting chain of $(C_{1-3})$alkyl;
B is O or S;
n is 0 or 1;
wherein when n is 0:
Ring C is 6- or 10-membered aryl or 5- or 6-membered heterocycle having from 1 to 4 heteroatoms selected from the group consisting of O, N, and S,
  said aryl and said heterocycle being optionally substituted with from 1 to 4 substituents selected from the group consisting of:
    halogen and $(C_{1-6})$alkyl optionally substituted with OH;
  and E is selected from:
    (i) $CONR^{12}R^{13}$ wherein $R^{12}$ and $R^{13}$ is each independently H, $SO_2(C_{1-6})$alkyl, $(C_{1-6})$alkyl-COOH, $(C_{1-6})$alkyl-$(C_{3-7})$cycloalkyl said cycloalkyl being optionally substituted with COOH;
    (ii) $CONHNR^{14}R^{15}$ wherein $R^{14}$ and $R^{15}$ is each independently H or $(C_{1-6})$alkyl optionally substituted with COOH;

(iii) NR$^{16}$COR$^{17}$ wherein R$^{16}$ is H or (C$_{1-6}$)alkyl optionally substituted with COOH or (C$_{6-10}$)aryl-COOH; and R$^{17}$ is (C$_{2-4}$)alkenyl-COOH, (C$_{3-7}$)cycloalkyl-COOH, NH(C$_{1-6}$)alkyl-COOH; (C$_{1-6}$)alkyl optionally substituted with COOH; or (C$_{1-6}$)alkyl-(C$_{3-7}$)cycloalkyl said cycloalkyl being optionally substituted with COOH;

(iv) NR$^{18}$SO$_2$(C$_{1-6}$)alkyl wherein R$^{18}$ is H or (C$_{1-6}$)alkyl;

(v) SO$_2$NR$^{19}$R$^{20}$ wherein R$^{19}$ is H or (C$_{1-6}$)alkyl; and R$^{20}$ is (C$_{1-6}$)alkyl optionally substituted with COOH; and (vi) SO$_2$R$^{21}$ wherein R$^{21}$ is (C$_{1-6}$)alkyl;

or when n is 1:

Ring C is as defined above; and

E is a single bond or a connecting group selected from:

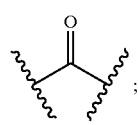
(vii)

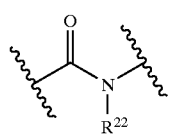
(viii)

wherein R$^{22}$ is H or (C$_{1-6}$)alkyl;

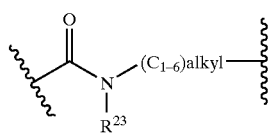
(ix)

wherein R$^{23}$ is H or (C$_{1-6}$)alkyl;

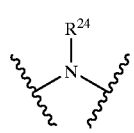
(x)

wherein R$^{24}$ is H or (C$_{1-6}$)alkyl;

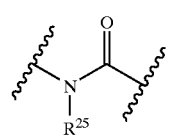
(xi)

wherein R$^{25}$ is H or (C$_{1-6}$)alkyl;

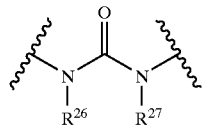
(xii)

wherein R$^{26}$ and R$^{27}$ is each H or (C$_{1-6}$)alkyl;

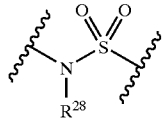
(xiii)

wherein R$^{28}$ is H or (C$_{1-6}$)alkyl;

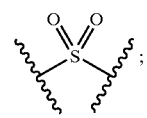
(xiv)

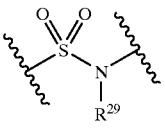
(xv)

wherein R$^{29}$ is H or (C$_{1-6}$)alkyl; and

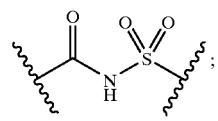
(xvi)

and

Ring D is a 6- or 10-membered aryl or a 5- or 6-membered heterocycle having from 1 to 4 heteroatoms selected from the group consisting of O, N, and S, said aryl and said heterocycle being optionally substituted with from 1 to 5 substituents selected from:

halogen, NH$_2$, NO$_2$, COOH, OH, COO(C$_{1-6}$) alkyl, (C$_{1-6}$)alkoxy, (C$_{2-4}$)alkenyl-COOH, (C$_{3-7}$)cycloalkyl-COOH and (C$_{1-6}$)alkyl optionally substituted with COOH or OH;

or a salt or a prodrug thereof.

According to a second aspect of the invention, there is provided a pharmaceutical composition for the treatment or prevention of HIV infection, comprising a compound of formula I, as described herein, or a pharmaceutically acceptable salt thereof, and a pharmaceutically acceptable carrier.

According to a third aspect of the invention, there is provided a method for the treatment or prevention of HIV infection, comprising administering to a patient an HIV inhibiting amount of a compound of formula I, a pharmaceutically acceptable salt thereof, or a pharmaceutical composition as described herein.

According to a fourth aspect of the invention, there is provided a method for treating or preventing HIV infection comprising administering a compound of formula I, as described herein, or a pharmaceutically acceptable salt thereof, and a pharmaceutically acceptable carrier, in combination with an antiretroviral drug.

According to a fifth aspect of the invention, there is provided a method for preventing perinatal transmission of HIV-1 from mother to baby, comprising administering a compound of formula I, as described herein, or a pharmaceutically acceptable salt thereof, and a pharmaceutically acceptable carrier, to the mother before giving birth.

According to a sixth aspect of the invention, there is provided the use of a compound of formula I, as described herein, for the manufacture of a medicament for the treatment or prevention of HIV infection.

DETAILED DESCRIPTION OF THE INVENTION

Definitions

The following definitions apply unless otherwise noted:

As used herein, the terms "$(C_{1-4})$alkyl" and "$(C_{1-6})$ alkyl", either alone or in combination with another radical, are intended to mean acyclic straight or branched alkyl radicals containing from one to four or from one to six carbon atoms respectively. Examples of such radicals include methyl, ethyl, propyl, isopropyl, butyl, sec-butyl, tert-butyl, hexyl, 1-methylethyl, 1-methylpropyl, 2-methylpropyl, 1,1-dimethylethyl.

As used herein, the terms "$(C_{3-4})$cycloalkyl" and "$(C_{3-7})$ cycloalkyl", either alone or in combination with another radical, are intended to mean saturated cyclic hydrocarbon radicals containing from three to four or from three to seven carbon atoms respectively. Examples of such radicals include cyclopropyl, cyclobutyl, cyclopentyl, cyclohexyl, and cycloheptyl.

As used herein, the terms "$(C_{1-6})$alkoxy" or "$O(C_{1-6})$ alkyl" are used interchangeably and are intended to mean acyclic alkyl radicals, containing from one to six carbon atoms, covalently bonded to an oxygen atom.

As used herein, the term "6- or 10-membered aryl", either alone or in combination with another radical means aromatic radical containing six or ten carbon atoms, for example phenyl or naphthyl.

As used herein, the term "heterocycle" or "Het", either alone or in combination with another radical, means a monovalent radical derived by removal of a hydrogen from a five-, six-, or seven-membered saturated or unsaturated (including aromatic) heterocycle containing from one to four heteroatoms selected from nitrogen, oxygen and sulfur. Furthermore, "Het" as used herein, means a heterocycle as defined above fused to one or more other cycle, be it a heterocycle or any other cycle. The heterocycles may be substituted. Examples of such substituents include, but are not limited to, halogen, amines, hydrazines and N-oxido. Examples of suitable heterocycles include: pyrrolidine, tetrahydrofuran, thiazolidine, pyrrole, thiophene, diazepine, 1H-imidazole, isoxazole, thiazole, tetrazole, piperidine, 1,4-dioxane, 4-morpholine, pyridine, pyrimidine, thiazolo[4,5-b]-pyridine, quinoline, or indole, or the following heterocycles:

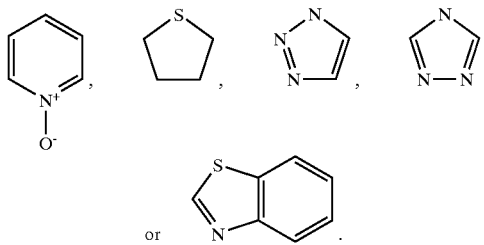

As used herein, the term "halo" means a halogen atom and includes fluorine, chlorine, bromine and iodine.

As used herein, the term "haloalkyl" is intended to mean an alkyl that is described above in which each hydrogen atom may be successively replaced by a halogen atom, for example $CH_2Br$ or $CF_3$.

As used herein, the term "pharmaceutically acceptable salt" includes those derived from pharmaceutically acceptable bases and is non-toxic. Examples of suitable bases include choline, ethanolamine and ethylenediamine. $Na^+$, $K^+$, and $Ca^{++}$ salts are also contemplated to be within the scope of the invention (also see Pharmaceutical salts, Birge, S. M. et al., J. Pharm. Sci., (1977), 66, 1–19, incorporated herein by reference).

As used herein, the term "prodrug" refers to pharmacologically acceptable derivatives, such that the resulting biotransformation product of the derivative is the active drug, as defined in compounds of formula I. Examples of such derivatives include, but are not limited to, esters and amides. (see Goodman and Gilman in The Pharmacological Basis of Therapeutics, $9^{th}$ ed., McGraw-Hill, Int. Ed. 1995, "Biotransformation of Drugs, p 11–16, incorporated herein by reference).

Preferred Embodiments

Preferably, compounds of the present invention have the following formula:

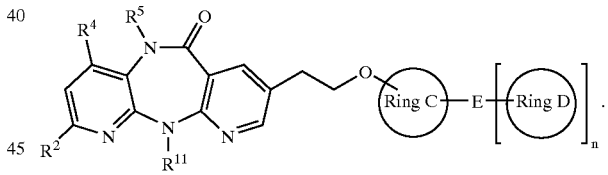

Preferably, $R^2$ is selected from: H, $(C_{1-4})$alkyl, halo, haloalkyl, OH, or $(C_{1-6})$alkoxy. More preferably, $R^2$ is H, Me, OMe, or halo. Most preferably, $R^2$ is H, F or Cl. Even most preferably, $R^2$ is H.

Preferably, $R^4$ is H.

Preferably, $R^5$ is Me.

Preferably, $R^{11}$ is H, Et or $(C_{3-4})$ cycloalkyl. More preferably, $R^{11}$ is Et or cyclopropyl. Most preferably, $R^{11}$ is Et.

When n=0, preferably, ring C is phenyl optionally substituted with from 1 to 2 substituents selected from the group consisting of:

halogen and $(C_{1-6})$alkyl optionally substituted with OH.

Still, preferably, ring C is phenyl optionally substituted with from 1 to 2 substituents selected from the group consisting of: halogen and $(C_{1-6})$alkyl.

More preferably, Ring C is phenyl optionally substituted with $(C_{1-6})$alkyl.

Still when n is 0, preferably, E is selected from the group consisting of:

(i) CONHSO$_2$(C$_{1-6}$)alkyl, CONH(C$_{1-6}$)alkyl-COOH, or CONH(C$_{1-6}$)alkyl-(C$_{3-7}$)cycloalkyl-COOH;

(ii) CONHNH$_2$, CONHNHMe, or CONHNHCH$_2$COOH;

(iii) NR$^{16}$COR$^{17}$ wherein R$^{16}$ is H or (C$_{1-6}$)alkyl optionally substituted with COOH or (C$_{6-10}$)aryl-COOH; and R$^{17}$ is (C$_{2-4}$)alkenyl-COOH, (C$_{3-7}$)cycloalkyl-COOH, NH(C$_{1-6}$)alkyl-COOH; (C$_{1-6}$)alkyl-(C$_{3-7}$)cycloalkyl-COOH; or (C$_{1-6}$)alkyl optionally substituted with COOH;

(iv) NHSO$_2$Me;

(v) SO$_2$NHCH$_2$COOH; and (vi) SO$_2$Me.

More preferably, E is selected from the group consisting of:

(i) CONHSO$_2$(C$_{1-6}$)alkyl, CONH(C$_{1-6}$)alkyl-COOH, or CONH(C$_{1-6}$)alkyl-(C$_{3-7}$)cycloalkyl-COOH;

(ii) CONHNH$_2$, CONHNHMe, or CONHNHCH$_2$COOH;

(iii) NR$^{16}$COR$^{17}$ wherein R$^{16}$ is H or (C$_{1-6}$)alkyl optionally substituted with COOH or (C$_{6-10}$)aryl-COOH; and R$^{17}$ is (C$_{2-4}$)alkenyl-COOH, (C$_{3-7}$)cycloalkyl-COOH, NH(C$_{1-6}$)alkyl-COOH; (C$_{1-6}$)alkyl-(C$_{3-7}$)cycloalkyl-COOH; or (C$_{1-6}$)alkyl optionally substituted with COOH; and (iv) NHSO$_2$Me.

Still, when n=0, preferably, E is in the para position.

Alternatively, when n=1, preferably, Ring C is phenyl optionally substituted with from 1 or 2 substituents selected from the group consisting of: halogen and (C$_{1-6}$)alkyl optionally substituted with OH.

Alternatively, when n=1, preferably, Ring C is phenyl optionally substituted with from 1 or 2 substituents selected from the group consisting of: halogen and (C$_{1-6}$)alkyl.

More preferably, Ring C is

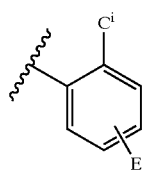 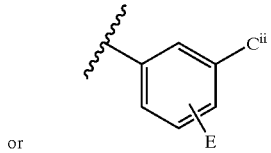

wherein C$^i$ is (C$_{1-6}$)alkyl and C$^{ii}$ is H, halogen, or (C$_{1-6}$)alkyl. Preferably, C$^i$ is CH$_3$. Preferably, C$^{ii}$ is H, Cl, or CH$_3$. Most preferably, C$^{ii}$ is H.

Still, when n is 1, E is a single bond or a connecting group selected from:

(vii)

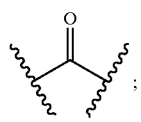

(viii)

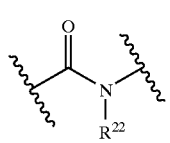

wherein R$^{22}$ is H or (C$_{1-6}$)alkyl;

(ix)

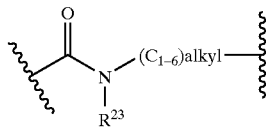

wherein R$^{23}$ is H or (C$_{1-6}$)alkyl;

(x)

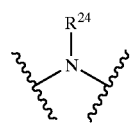

wherein R$^{24}$ is H or (C$_{1-6}$)alkyl;

(xi)

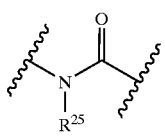

wherein R$^{25}$ is H or (C$_{1-6}$)alkyl;

(xii)

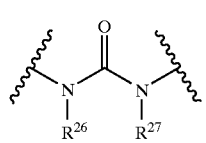

wherein R$^{26}$ and R$^{27}$ is each H or (C$_{1-6}$)alkyl;

(xiii)

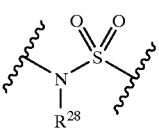

wherein R$^{28}$ is H or (C$_{1-6}$)alkyl;

(xiv)

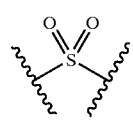

and (xv)

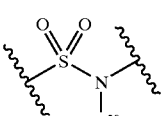

wherein R$^{29}$ is H or (C$_{1-6}$)alkyl;

Alternatively, E is preferably a single bond or a connecting group selected from:

(vii) 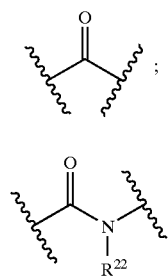

(viii) 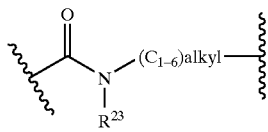

wherein $R^{22}$ is H or Me;

(ix) 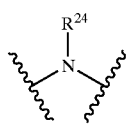

wherein $R^{23}$ is H or Me;

(x) 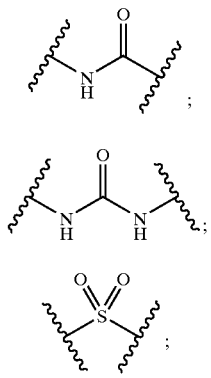

wherein $R^{24}$ is H or Me;

(xi) 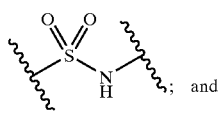

(xii) 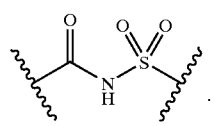

(xiv)

(xv)

(xvi)

Most preferably, E is a connecting group selected from:

(vii) 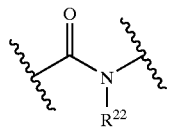

wherein $R^{22}$ is H or Me;

x) 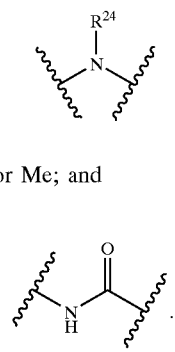

wherein $R^{24}$ is H or Me; and xi) 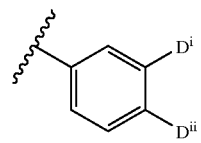

Still, when n is 1, preferably, E is in the para position.

Preferably, Ring D is phenyl or 5- or 6-membered heterocycle having from 1 to 4 heteroatoms selected from the group consisting of O, N, and S, said phenyl and said heterocycle being optionally substituted with from 1 to 4 substituents selected from:

halogen, $NH_2$, $NO_2$, COOH, OH, $COO(C_{1-6})$alkyl, $(C_{1-6})$alkoxy, $(C_{2-4})$alkenyl-COOH; $(C_{3-7})$ cycloalkyl-COOH; or $(C_{1-6})$alkyl optionally substituted with COOH or OH.

Alternatively, Ring D is preferably phenyl or 5- or 6-membered heterocycle having from 1 to 4 heteroatoms selected from the group consisting of O, N, and S, said phenyl and said heterocycle being optionally substituted with from 1 to 4 substituents selected from:

halogen, $NH_2$, $NO_2$, COOH, OH, $(C_{1-6})$alkoxy, $(C_{2-4})$ alkenyl-COOH; $(C_{3-7})$ cycloalkyl-COOH; or $(C_{1-6})$ alkyl optionally substituted with COOH or OH.

More preferably, Ring D is phenyl optionally substituted with 1 to 3 substituents selected from the group consisting of: COOH, OH, $(C_{1-6})$alkyl-COOH, or $(C_{1-6})$ alkyl(OH)-COOH, $(C_{1-6})$alkyl, halogen, $(C_{1-6})$alkoxy, $NH_2$, or $NO_2$.

Still more preferably, Ring D is phenyl optionally substituted with 1 or 2 substituents selected from the group consisting of: COOH, $CH_2COOH$, $CH_2CH_2COOH$, $CH_3$, F, Cl, OMe, $NO_2$, $NH_2$, or OH.

Most preferably, Ring D is:

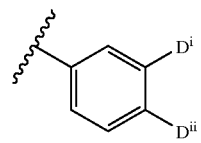

wherein $D^i$ is COOH, $(C_{1-6})$alkyl optionally substituted with COOH, or halogen, and $D^{ii}$ is COOH, OH, $NH_2$, halogen, $(C_{1-6})$alkyl optionally substituted with COOH, with the proviso that $D^i$ and $D^{ii}$ are not both COOH. Preferably, $D^i$ is COOH, —$CH_2COOH$, Me, F, or Cl. Preferably, $D^{ii}$ is OH, $NH_2$, F, Cl, —$CH_2COOH$ or COOH.

Even most preferably, Ring D is phenyl mono-substituted with COOH, CH$_2$COOH, or CH$_2$CH$_2$COOH at the para or meta position.

Alternatively preferably, Ring D is thiophene, furan, thiazole, oxazole, isoxazole, pyrazole, triazole, imidazole, pyridine, pyridine-N-oxide, pyridinone, pyrimidine, or tetrazole
 each being optionally substituted with from 1 to 2 substituents selected from: halogen, NH$_2$, COOH, OH, (C$_{1-6}$)alkoxy, (C$_{1-6}$)alkyl optionally substituted with COOH or OH.

Alternatively preferably, Ring D is thiophene, furan, thiazole, oxazole, isoxazole, pyrazole, triazole, imidazole, pyridine, pyridine-N-oxide, pyridinone or pyrimidine each being optionally substituted as above.

Alternatively preferably, Ring D is thiophene, furan or thiazole, each optionally substituted with from 1 to 3 substituents selected from:NH$_2$, COOH, and (C$_{1-6}$)alkyl optionally substituted with COOH. More preferably, the thiophene, furan or thiazole are unsubstituted or mono- or di-substituted with COOH, —CH$_2$—COOH, or NH$_2$.

Alternatively preferably, Ring D is imidazole optionally substituted with from 1 to 2 substituents selected from: (C$_{1-6}$)alkyl. More preferably, the imidazole is unsubstituted or mono-substituted with Me.

Alternatively preferably, Ring D is pyrazole optionally substituted with from 1 to 2 substituents selected from: COOH, (C$_{1-6}$)alkyl optionally substituted with COOH.

More preferably, the pyrazole is unsubstituted or mono- or di-substituted with Me, COOH or —CH$_2$—COOH.

Alternatively preferably, Ring D is triazole substituted with COOH.

Alternatively preferably, Ring D is isoxazole optionally substituted with COOH.

Alternatively preferably, Ring D is oxazole.

Alternatively preferably, Ring D is pyridine or pyridine-N-oxide optionally substituted with 1 to 3 substituents selected from: COOH, (C$_{1-6}$)alkyl, halogen, NH$_2$, or OH. More preferably, the pyridine or pyridine-N-oxide is mono- or di-substituted with Me, Cl, NH$_2$, or OH. Most preferably, ring D is pyridine-N-oxide.

Alternatively preferably, Ring D is pyrimidine.

Alternatively preferably, Ring D is pyridinone optionally substituted with 1 to 2 substituents selected from: (C$_{1-6}$) alkyl optionally substituted with COOH. More preferably, the pyridinone is mono-substituted on the nitrogen atom with —CH$_2$—COOH.

Alternatively preferably, Ring D is tetrazole.

Also comprised within the preferred embodiments of the present invention is each specific compound described in Tables 1 to 4.

Antiviral Activity

The compounds of the present invention are effective inhibitors of HIV-1 wild type reverse transcriptase as well as the clinically significant double mutant K103N/Y181C. The compounds also may be effective inhibitors of, for example, the single mutant enzymes Y181C, V106A, and Y188C.

When administered in suitable dosage forms, they are useful in the treatment of AIDS, ARC and related disorders associated with HIV-1 infection. Another aspect of the invention, therefore, is a method for treating HIV-1 infection which comprises administering to a human being, infected by HIV-1, a therapeutically effective amount of a novel compound of formula I, as described above. Whether it be termed treatment or prophylaxis, the compounds may also be used to prevent perinatal transmission of HIV-1 from mother to baby, by administration to the mother prior to giving birth.

The compounds of formula I may be administered in single or divided doses by the oral or parenteral routes. A suitable oral dosage for a compound of formula I would be in the range of about 0.5 mg to 3 g per day. A preferred oral dosage for a compound of formula I would be in the range of about 100 mg to 800 mg per day for a patient weighing 70 kg. In parenteral formulations, a suitable dosage unit may contain from 0.1 to 250 mg of said compounds, preferably 1 mg to 200 mg. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations, which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The compounds of formula I can be used in combination with an antiretroviral drug known to one skilled in the art, as a combined preparation useful for simultaneous, separate or sequential administration for treating or preventing HIV infection in an individual. Examples of antiretroviral drugs that may be used in combination therapy with compounds of formula I, include but are not limited to, nucleoside/nucleotide reverse transcriptase inhibitors (such as AZT and Tenofovir), non-nucleoside reverse transcriptase inhibitors (such as Nevirapine), protease inhibitors (such as Ritonavir), viral fusion inhibitors (such as T-20), CCR5 antagonists (such as SCH-351125), CXCR4 antagonists (such as AMD-3100), integrase inhibitors (such as L-870,810), TAT inhibitors, other investigational drugs (such as PRO-542, BMS-806, TMC-114 or AI-183), antifungal or antibacterial agents (such as fluconazole), and immunomodulating agents (such as Levamisole). Moreover, a compound of formula I can be used with another compound of formula I.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered by suppository.

Methodology and Synthesis

Exemplary reaction schemes, disclosed in WO 01/96338, the contents of which are incorporated herein by reference, show the many synthetic routes to the tricyclic core illustrated hereinafter. The compounds of the present invention may be made using the skills of a synthetic organic chemist. Exemplary reaction schemes are illustrated in Schemes 1 to 8. Substituents $R^2$, $R^4$, $R^5$, and $R^{11}$ are as defined herein.

Schemes 1 to 3 show the methods for the preparation of aryl- and heteroaryl-phenols.

Briefly, protected phenol 1(i) can be coupled to a heterocycle or an aryl, for example via a Suzuki coupling, to give 1(ii), which is deprotected if necessary, to give 1(v). Alternatively, phenol 1(iv) can be coupled to aryl or heterocyclic derivative 1(iii) to give 1(v).

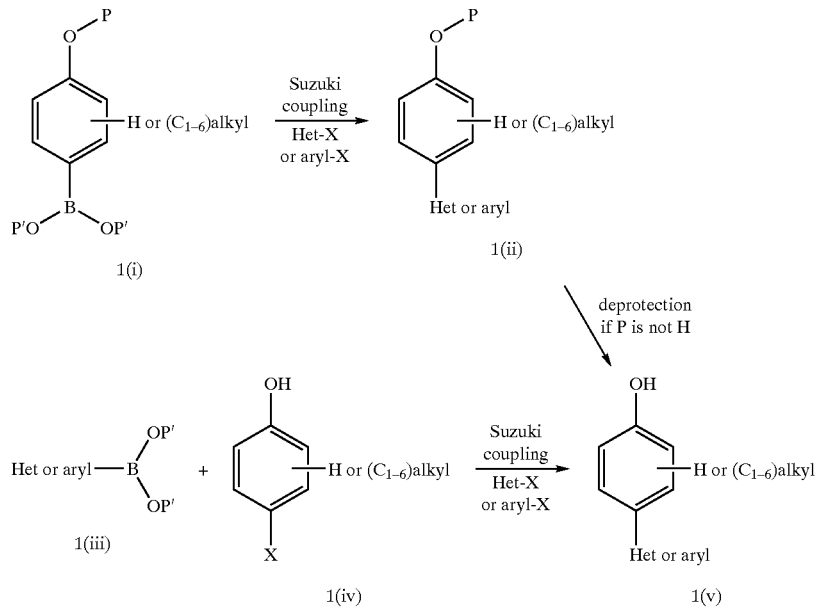

Scheme 1 wherein P or P' is a hydroxy protecting group and X is a leaving group

Scheme 2

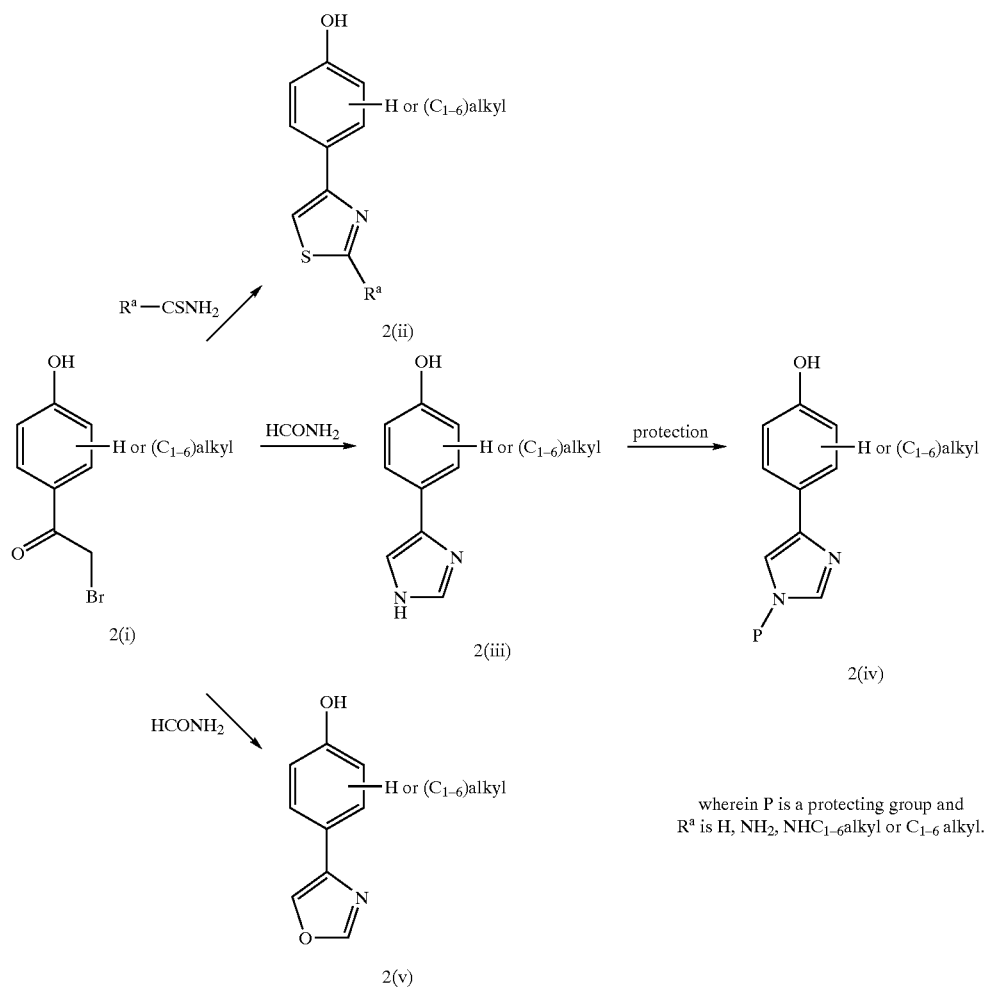

wherein P is a protecting group and
$R^a$ is H, $NH_2$, $NHC_{1-6}$alkyl or $C_{1-6}$ alkyl.

Briefly, the α-bromomethyl ketone 2(i) is condensed with an appropriate reagent, for example formamide, or $R^aCSNH_2$, to form the corresponding heterocyclic compounds 2(ii), 2(iii) or 2(v). If necessary, the heterocycle may be protected, giving 2(iv), before condensation with alcohol 4(i) shown below.

Scheme 3

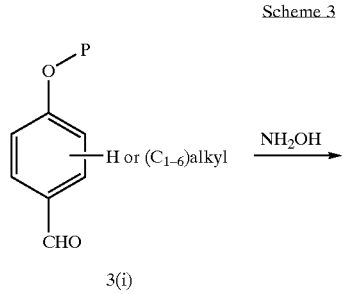

-continued

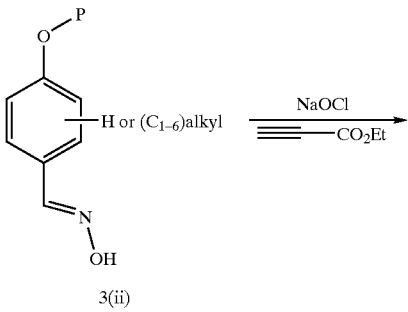

-continued

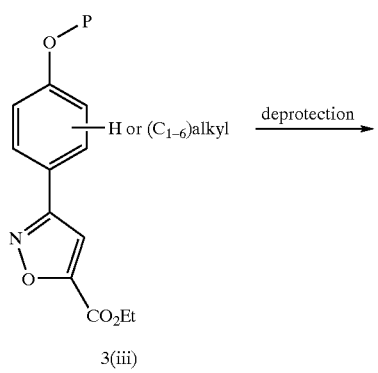

3(iii)

Alternatively, a heterocyclic moiety can be introduced by an in situ heterocycle formation. Aldehyde 3(i) can be condensed with NH$_2$OH to give 3(ii). Further condensation with an alkynyl derivative gives the heterocycle 3(ii), which thereafter can be deprotected to give 3(iv).

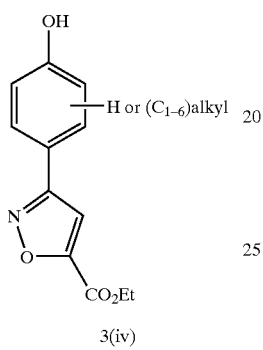

3(iv)

Scheme 4 shows a general method for the coupling of substituted phenols to the tricyclic core.

Scheme 4

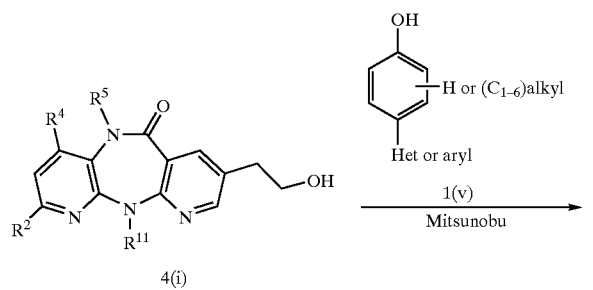

4(i)

-continued

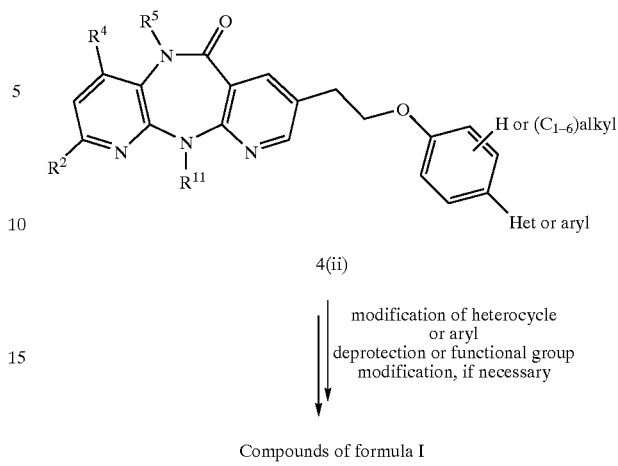

4(ii)

↓ modification of heterocycle
 or aryl
 deprotection or functional group
 modification, if necessary Compounds of formula I Generally, phenol 1(v) can be condensed with the alcohol 4(i) using, for example, a Mitsunobu type reaction, to give 4(ii). Thereafter, the heterocycle moiety can be further modified by, for example oxidation, or the heterocycle may be deprotected to give compounds of formula I.

Alternatively, Schemes 5 to 8 show the coupling of the tricyclic core to phenols bearing substituents which are precursors of the E–D portion of compounds of formula I.

Scheme 5

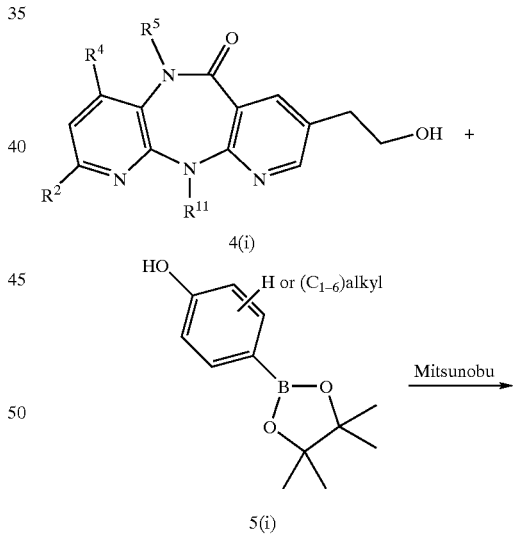

4(i)

5(i)

Mitsunobu →

19
-continued
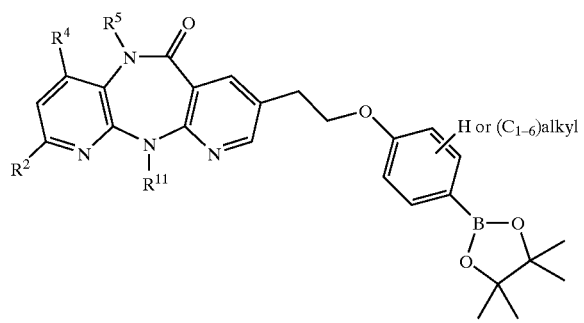
5(ii)
Suzuki coupling | Het-X or aryl-X
↓
20
-continued
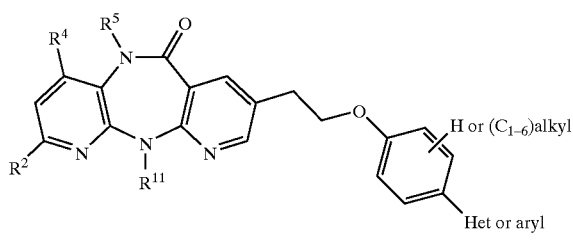
4(ii)
Alternatively, a boron-containing compound 5(i) can be condensed with the alcohol 4(i) to give 5(ii). Thereafter, the heterocyclic or aryl moiety can be introduced by a Suzuki coupling to give 4(ii).
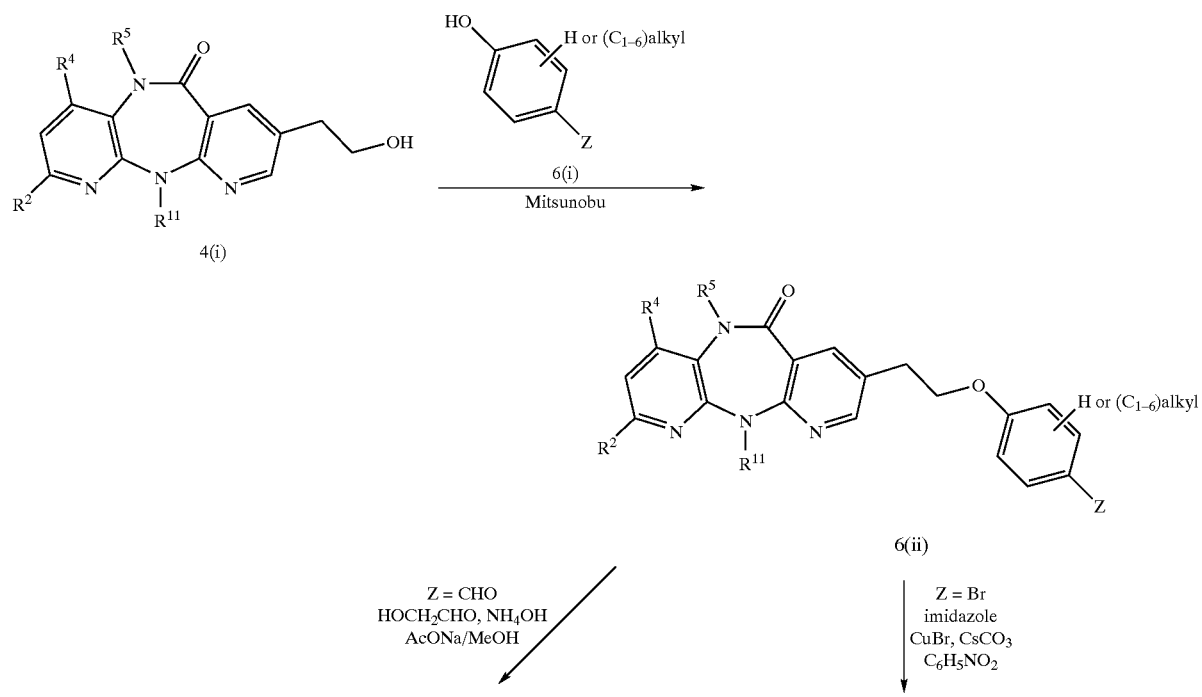

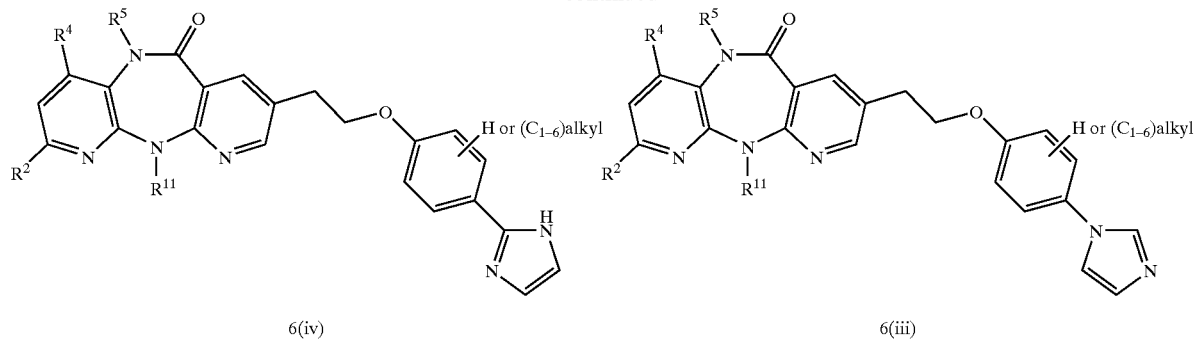

6(iv)                                          6(iii)

Alternatively, 6(ii) can be produced by a condensation reaction as described above, in which Z is either an aldehyde or a halogen. The heterocycle moiety can then be introduced by direct coupling to produce 6(iii) or via an in situ synthesis to give 6(iv).

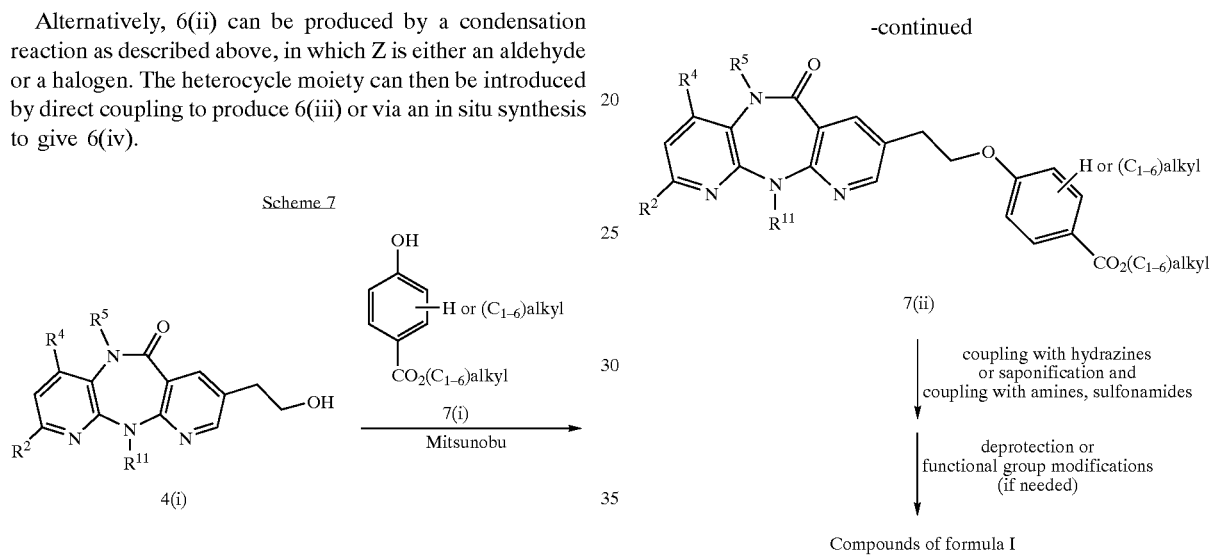

Alternatively, 4(i) and 7(i) can be condensed using a Mitsunobu reaction to give 7(ii). Thereafter, coupling, saponification or functional group modification can be used to convert 7(ii) into compounds of formula I.

Scheme 8

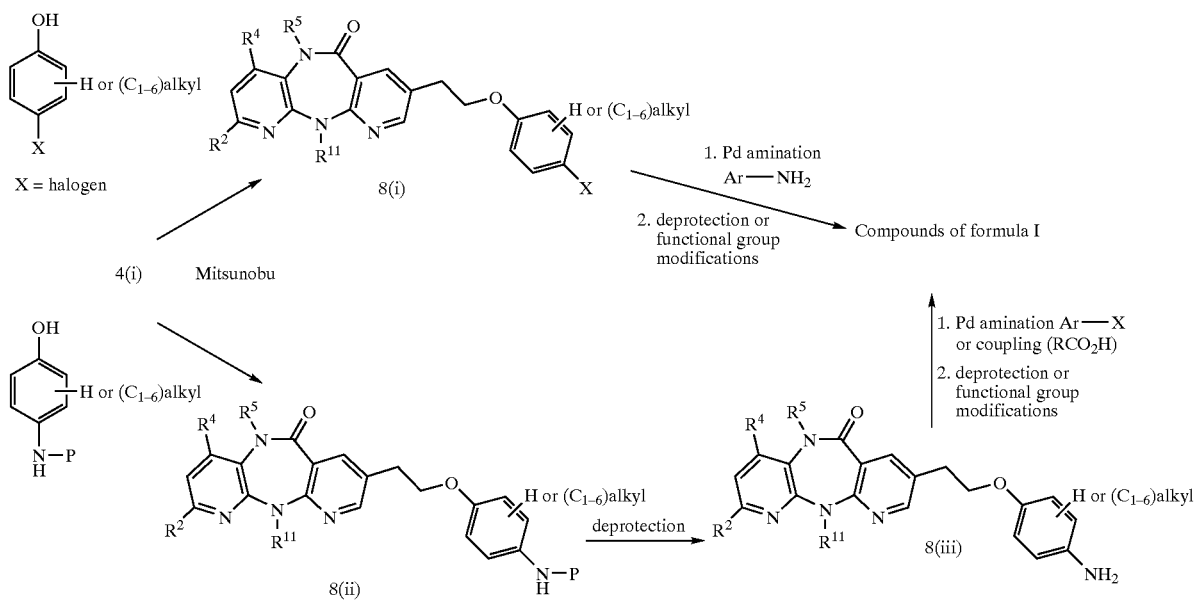

In another example, 8(i) can be converted into its corresponding amine by a palladium-mediated amination reaction followed by either deprotection or function group modifications, to give compounds of formula I. Alternatively, the amine in 8(ii) can be converted into compounds of formula I by a series of deprotections and/or functional group modifications.

Utilizing the Reverse Transcriptase (RT) Assay described below, compounds were tested for their ability to inhibit the RNA-dependent DNA polymerase activity of HIV-1 RT. Certain specific compounds described in the Examples and in Tables 1–4, were so tested. The results of this testing appear in Table 5 as ranges of $IC_{50}$ (nM) and $EC_{50}$ (nM).

EXAMPLES

The present invention is illustrated in further detail by the following non-limiting examples. All reactions were performed in a nitrogen or argon atmosphere unless otherwise stated. Temperatures are given in degrees Celsius. Solution percentages or ratios express a volume to volume relationship, unless stated otherwise.

Abbreviations or symbols used herein include:

BINAP: 2,2'-Bis(diphenylphosphino)-1,1'-binaphthyl; Bis-Tris Propane: 1,3-Bis{tris(hydroxymethyl)-methylamino}propane; DCC: dicyclohexylcarbodiimide; DEAD: diethyl azodicarboxylate; DEPC: diethyl pyrocarbonate; DIAD: diisopropyl azodicarboxylate; DIEA: diisopropylethylamine; DMAP: 4-(dimethylamino)pyridine; DMF: dimethylformamide; DMSO: dimethylsulfoxide; Dppf: 1,1'-bis(diphenyl phosphino)ferrocene; DTT: dithiothreitol; EDTA: ethylenediaminetetraacetate; ES MS: electron spray mass spectrometry; Et: ethyl; $Et_2O$: diethyl ether; EtOAc: ethyl acetate; EtOH: ethanol; GSH: reduced glutathione; HPLC: high performance liquid chromatography; iPr: isopropyl; MCPBA: meta-chloroperbenzoic acid; Me: methyl; MeCN: acetonitrile; MeOH: methanol; MES: 2-(n-morpholino)ethanesulfonic acid; MWCO: molecular weight cut-off; NBS: N-bromosuccinimide; OBG: n-Octyl-β-D-glucoside. $Pd_2(dba)_3$: Tris (dibenzylideneacetone) dipalladium (0); $PdCl_2(dppf)$: [1,1'-bis(diphenylphosphino)ferrocene]palladium dichloride; PFU: plaque forming units; Ph: phenyl; SDS-PAGE: sodium dodecyl sulfate-polyacrylamide gel electrophoresis; TBE: tris-borate-EDTA; TBTU: 2-(1H-benzotriazol-1-yl)-N,N,N',N'-tetramethyluronium tetrafluoroborate; TFA: trifluoroacetic acid; THF: tetrahydrofuran; UMP: uridine 5'-monophosphate; and UTP: uridine 5'-triphosphate.

Synthesis

The following examples illustrate methods for preparing compounds of the invention.

Example 1 (Entry 1013)

4'-[2-(11-Ethyl-6,11-dihydro-5-methyl-6-oxo-5H-dipyrido[3,2-b:2',3'-e][1,4]diazepin-8-yl)ethoxy]-3'-methyl-[1,1'-biphenyl]-3-carboxylic acid a) 2-(4-Methoxy-3-methylphenyl)-4,4,5,5-tetramethyl-1,3,2-dioxoborolane A mixture of bis(pinacolato)diborane (10.7 g, 42.1 mmol), 4-bromo-1-methoxy-2-methylbenzene (7.70 g, 38.3 mmol) and KOAc (10.9 g, 114 mmol) in DMSO (200 mL) was degassed with argon for 10 min. $PdCl_2$dppf (1:1 complex with $CH_2Cl_2$, 2.50 g, 3.06 mmol) was next added and the reaction mixture was heated to 80° C. for 24 h. The reaction mixture was diluted with water and extracted with $C_6H_6$ (3×). The combined organic layers were washed with brine, dried ($MgSO_4$), filtered and concentrated under reduced pressure. The residue was purified by flash chromatography (Hexane:EtOAc, 95:5) to yield the title compound (5.1 g, 54% yield) as a colorless oil.

b) Methyl 4'-methoxy-3'-methyl-[1,1'-biphenyl]-3-carboxylate

To a degassed (argon, 10 min) mixture of 2-(4-methoxy-3-methylphenyl)-4,4,5,5-tetramethyl-1,3,2-dioxoborolane (500 mg, 2.01 mmol), 3-bromobenzoic acid (446 mg, 2.22 mmol), and aqueous 1 M $Na_2CO_3$ solution (6.3 mL) in DMSO (20 mL) was added $PdCl_2$dppf (1:1 complex with $CH_2Cl_2$, 132 mg, 0.16 mmol). The reaction mixture was heated to 80° C. for 12 h. The cooled mixture was acidified with aqueous 1 N HCl solution and extracted with EtOAc. The organic layer was washed with brine, dried (MgSO$_4$), filtered and concentrated under reduced pressure. The crude resulting acid was dissolved in Et$_2$O (150 mL) and was treated with excess ethereal CH$_2$N$_2$ solution (ca. 0.6 M). The mixture was concentrated under reduced pressure. The residue was purified by flash chromatography (Hexane:EtOAc, 20:1) to give the title compound (350 mg, 68% yield).

c) Methyl 4'-hydroxy-3'-methyl-[1,1'-biphenyl]-3-carboxylate

A 1.0 M BBr$_3$ solution in CH$_2$Cl$_2$ (3.4 mL, 3.40 mmol) was added to an ice-cold solution of methyl 4'-methoxy-3'-methyl-[1,1'-biphenyl]-3-carboxylate (345 mg, 1.35 mmol) in CH$_2$Cl$_2$ (13 mL). The reaction mixture was stirred at 25° C. for 2 h then was cooled to 0° C. MeOH (5 mL) was added and the mixture was stirred at 0° C. for 15 min then was extracted with CH$_2$Cl$_2$ (2×). The combined organic layers were washed with brine, dried (MgSO$_4$), filtered and concentrated under reduced pressure. The residue was purified by flash chromatography (EtOAc:Hexane, 10 to 15%) to yield the title compound (278 mg, 85% yield) as a white solid.

d) Methyl 4'-[2-(11-ethyl-6,11-dihydro-5-methyl-6-oxo-5H-dipyrido[3,2-b:2',3'-e][1,4]diazepin-8-yl)ethoxy]-3'-methyl-[1,1'-biphenyl]-3-carboxylate A solution of DEAD (65 μL, 0.41 mmol) in THF (0.15 mL) was added over 2 h to an ice-cold solution of 11-ethyl-5,11-dihydro-8-(2-hydroxyethyl)-5-methyl-6H-dipyrido[3,2-b:2',3'-e][1,4]diazepin-6-one (100 mg, 0.34 mmol: prepared according to the methods described in WO 01/96338, which is hereby incorporated by reference), methyl 4'-hydroxy-3'-methyl-[1,1'-biphenyl]-4-carboxylate (100 mg, 0.41 mmol) and PPh$_3$ (108 mg, 0.41 mmol) in THF (4.0 mL). The reaction mixture was stirred at 25° C. for 16 h. An additional amount of DEAD (30 μL, 0.19 mmol) was added and the reaction mixture was stirred at 25° C. for 16 h then was concentrated under reduced pressure. The residue was purified by flash chromatography (toluene:EtOAc, 85:15) to give the title compound (136 mg, 78% yield) as white solid.

e) 4'-[2-(11-Ethyl-6,11-dihydro-5-methyl-6-oxo-5H-dipyrido[3,2-b:2',3'-e][1,4]diazepin-8-yl)ethoxy]-3'-methyl-[1,1'-biphenyl]-3-carboxylic acid An aqueous 1 N NaOH solution (0.78 mL, 0.78 mmol) was added to a solution of methyl 4'-[2-(11-ethyl-6,11-dihydro-5-methyl-6-oxo-5H-dipyrido[3,2-b:2',3'-e][1,4]diazepin-8-yl)ethoxy]-3'-methyl-[1,1'-biphenyl]-3-carboxylate (136 mg, 0.26 mmol) in THF (2 mL) and MeOH (1.0 mL). The mixture was stirred at 25° C. for 1 h. The resulting solution was acidified with aqueous 1 N HCl solution and the mixture was extracted with EtOAc (3×). The combined organic layers were washed with brine, dried (MgSO$_4$), filtered and concentrated under reduced pressure to give the title compound 1013 (108 mg, 77% yield) as a white solid.

Example 2 (Entry 1034)

4-Amino-4'-[2-(11-ethyl-6,11-dihydro-5-methyl-6-oxo-5H-dipyrido[3,2-b:2',3'-e][1,4]diazepin-8-yl)ethoxy]-3'-methyl-[1,1'-biphenyl]-3-carboxylic acid a) 2-(4-Hydroxy-3-methylphenyl)-4,4,5,5-tetramethyl-1,3,2-dioxoborolane A mixture of bis(pinacolato)diborane (19.6 g, 77.0 mmol), 4-bromo-2-methylphenol (12.00 g, 64.2 mmol) and KOAc (18.9 g, 192 mmol) in DMSO (300 mL) was degassed with argon for 1 h. PdCl$_2$dppf (1:1 complex with CH$_2$Cl$_2$, 7.04 g, 9.6 mmol) was next added and the reaction mixture was heated to 80° C. for 10 h. The reaction mixture was diluted with EtOAc (1 L) and the resulting solution was washed with water (3×500 mL) and brine (500 mL), dried (MgSO$_4$), filtered and concentrated under reduced pressure. The residue was purified by flash chromatography (Hexane:EtOAc, 4:1) to give the title compound (6.76 g, 45% yield) as a yellow oil.

b) 2-{4-[2-(11-Ethyl-6,11-dihydro-5-methyl-6-oxo-5H-dipyrido[3,2-b:2',3'-e][1,4]diazepin-8-yl)ethoxy]-3-methylphenyl}-4,4,5,5-tetramethyl-1,3,2-dioxoborolane DIAD (1.93 mL, 9.80 mmol) was added dropwise to a solution of 11-ethyl-5,11-dihydro-8-(2-hydroxyethyl)-5-methyl-6H-dipyrido[3,2-b:2',3'-e][1,4]diazepin-6-one (2.44 g, 8.19 mmol), 2-(4-hydroxy-3-methylphenyl)-4,4,5,5-tetramethyl-1,3,2-dioxoborolane (2.30 g, 9.83 mmol) and PPh$_3$ (2.58 g, 9.82 mmol) in THF (33 mL) at 25° C. The reaction mixture was stirred at 25° C. for 72 h. The mixture was concentrated under reduced pressure. The residue was purified by flash chromatography (Hexane:EtOAc, 3:2) to give the title compound (3.11 g, 74% yield) as a white foam.

c) 4-Amino-4'-[2-(11-ethyl-6,11-dihydro-5-methyl-6-oxo-5H-dipyrido[3,2-b:2',3'-e][1,4]diazepin-8-yl)ethoxy]-3'-methyl-[1,1'-biphenyl]-3-carboxylic acid A mixture of 2-{4-[2-(11-ethyl-6,11-dihydro-5-methyl-6-oxo-5H-dipyrido[3,2-b:2',3'-e][1,4]diazepin-8-yl)ethoxy]-3-methylphenyl}-4,4,5,5-tetramethyl-1,3,2-dioxoborolane (160 mg, 0.31 mmol), methyl 5-bromo-2-aminobenzoate (143 mg, 0.62 mmol) and K$_3$PO$_4$ (247 mg, 1.17 mmol) in 1,4-dioxane (10 mL) was degassed with N$_2$ for 30 min. PdCl$_2$(dppf) (1:1 complex with CH$_2$Cl$_2$, 28.5 mg, 34.8 μmol) and dppf (21.6 mg, 38.9 μmol) were next added and the reaction mixture was heated under N$_2$ to 80° C. for 16 h. The cooled mixture was concentrated under reduced pressure and the residue was taken in EtOAc (50 mL). The organic layer was washed with water (10 mL) and brine (10 mL), dried (MgSO$_4$), filtered and concentrated under reduced pressure. The residue was purified by flash chromatography (EtOAc:Hexane, 1:1). The resulting methyl ester was dissolved in MeOH (2 mL) and THF (2 mL) and aqueous 1 N NaOH solution (2.0 mL, 2.0 mmol) were added. The mixture was stirred at 25° C. for 18 h then was concentrated under reduced pressure. The residual aqueous solution was diluted with aqueous 1 N NaOH solution (50 mL) and the resulting solution was washed with Et$_2$O (15 mL). The aqueous layer was rendered acidic with aqueous 1 N HCl solution and was extracted with EtOAc (3×30 mL). The combined organic were washed with water (15 mL) and brine (15 mL), dried (MgSO$_4$), filtered and concentrated under reduced pressure. The residue was purified by reverse phase HPLC (CombiPrep ODS-AQ 50×20 mm, 5μ, 120 A, MeCN/water+0.10% TFA) to provide the title compound 1034 (60 mg) as a yellow solid. The acid was treated with aqueous 0.1 N NaOH solution (1.14 mL, 1 equiv.) in water/MeCN (3:1, 5 mL) and the resulting solution was frozen and lyophilized to give the sodium salt of the title compound 1034 (56 mg, 33% yield) as a white solid.

Example 3 (Entry 1041)

3-{4-[2-(11-Ethyl-6,11-dihydro-5-methyl-6-oxo-5H-dipyrido[3,2-b:2',3'-e][1,4]diazepin-8-yl)ethoxy]-3-methylphenyl}-5-isoxazolecarboxylic acid a) 4-(Methoxymethoxy)-3-methylbenzaldehyde To a solution of 4-hydroxy-3-methylbenzaldehyde (900 mg, 6.61 mmol) in CH$_2$Cl$_2$ (19 mL) was added Et$_3$N (5.90 mL, 42.3 mmol) and chloromethyl methyl ether (2.00 mL, 26.3 mmol). The reaction was stirred at 25° C. for 16 h. The reaction mixture was diluted with EtOAc and was successively washed with aqueous 1 N HCl solution, aqueous saturated NaHCO$_3$ solution, water and brine, dried (MgSO$_4$), filtered and concentrated under reduced pressure. The residue was purified by flash chromatography (Hexane:EtOAc, 4:1) to give the title compound (630 mg, 53% yield) as a clear oil.

b) 4-(Methoxymethoxy)-3-methylbenzaldehyde oxime

Et$_3$N (1.68 mL, 12.0 mmol) and hydroxylamine hydrochloride (320 mg, 4.64 mmol) were added to a solution of 4-(methoxymethoxy)-3-methylbenzaldehyde (620 mg, 3.44 mmol) in 1,4-dioxane (12 mL). The reaction mixture was sonicated for 10 min and stirred at 25° C. for 3 d. The reaction mixture was diluted with EtOAc and successively washed with water and brine, dried (MgSO$_4$), filtered and concentrated under reduced pressure. The residue was purified by flash chromatography (Hexane:EtOAc, 3:1) to provide the title compound (580 mg, 86% yield) as a clear gum.

c) Ethyl 3-[4-(methoxymethoxy)-3-methyl phenyl]-5-isoxazolecarboxylate

Ethyl propiolate (0.60 mL, 5.88 mmol) and 6% W/V NaOCl solution in water (10.8 mL) were added to a solution of 4-(methoxymethoxy)-3-methylbenzaldehyde oxime (570 mg, 2.92 mmol) in THF (12 mL). The reaction mixture was stirred at 25° C. for 2 h then was diluted with EtOAc. The resulting solution was successively washed with aqueous 10% Na$_2$S$_2$O$_3$ solution, water and brine, dried (MgSO$_4$), filtered and concentrated under reduced pressure to yield the title compound (745 mg, 88% yield) as a yellow solid.

d) Ethyl 3-(4-hydroxy-3-methylphenyl)-5-isoxazolecarboxylate

A solution of ethyl 3-[4-(methoxymethoxy)-3-methylphenyl]-5-isoxazolecarboxylate (725 mg, 2.49 mmol) and aqueous 4 N HCl solution (6 mL) in THF (10 mL) was stirred at 25° C. for 16 h. The reaction mixture was diluted with EtOAc and successively washed with water and brine, dried (MgSO$_4$), filtered and concentrated under reduced pressure to give the title compound (434 mg, 70% yield) as a yellow solid.

e) Ethyl 3-{4-[2-(11-ethyl-6,11-dihydro-5-methyl-6-oxo-5H-dipyrido[3,2-b:2',3'-e][1,4]diazepin-8-yl)ethoxy]-3-methylphenyl}-5-isoxazolecarboxylate DEAD (55 μL, 0.35 mmol) was added over 30 min to a solution of 11-ethyl-5,11-dihydro-8-(2-hydroxyethyl)-5-methyl-6H-dipyrido[3,2-b:2',3'-e][1,4]diazepin-6-one (70.0 mg, 0.23 mmol), ethyl 3-(4-hydroxy-3-methylphenyl)-5-isoxazolecarboxylate (86.5 mg, 0.35 mmol) and PPh$_3$ (91.8 mg, 0.35 mmol) in THF (2 mL) at 25° C. The reaction mixture was stirred at 25° C. for 18 h. The mixture was concentrated under reduced pressure. The residue was purified by flash chromatography (CH$_2$Cl$_2$:EtOAc, 10:1) to give the title compound (55 mg, 45% yield).

f) 3-{4-[2-(11-Ethyl-6,11-dihydro-5-methyl-6-oxo-5H-dipyrido[3,2-b:2',3'-e][1,4]diazepin-8-yl)ethoxy]-3-methylphenyl}-5-isoxazolecarboxylic acid A solution of ethyl 3-{4-[2-(11-ethyl-6,11-dihydro-5-methyl-6-oxo-5H-dipyrido[3,2-b:2',3'-e][1,4]diazepin-8-yl)ethoxy]-3-methylphenyl}-5-isoxazolecarboxylate (50.0 mg, 0.090 mmol) and aqueous 1 N NaOH solution (0.90 mL, 0.90 mmol) in THF (2 mL) and MeOH (0.5 mL) was stirred at 25° C. for 1 h. The reaction mixture was concentrated under reduced pressure, acidified with aqueous 4 N HCl solution and extracted with EtOAc (1×) and CH$_2$Cl$_2$ (1×). The combined organic layers were washed with water and brine, dried (MgSO$_4$), filtered and concentrated under reduced pressure. The resulting solid was triturated with EtOAc/Hexane to give the title compound (40 mg, 85% yield) as a pale yellow solid. A 1 N NaOH solution (78 μL, 0.078 mmol) was added to a solution of the title compound (39.0 mg, 0.078 mmol) in THF (3 mL). After 45 min, the mixture was concentrated. The residue was dissolved in water and MeCN then the solution was frozen and lyophilized to give the corresponding sodium salt of the title compound 1041 (40.5 mg, 100% yield) as a white solid.

Example 4 (Entry 1046)

5-{4-[2-(11-Ethyl-6,11-dihydro-5-methyl-6-oxo-5H-dipyrido[3,2-b:2',3'-e][1,4]diazepin-8-yl)ethoxy]-3-methylphenyl}-2-furanecarboxylic acid a) 5-(4-Hydroxy-3-methylphenyl)-2-furanecarboxaldehyde Pd(PPh$_3$)$_4$ (69.3 mg, 0.06 mmol) was added to a degassed (N$_2$ for 15 min) solution of 4-bromo-2-methylphenol (225 mg, 1.20 mmol), 2-formylfuran-5-boronic acid (177 mg, 1.26 mmol) and aqueous 0.4 M Na$_2$CO$_3$ (6 mL) in MeCN (12 mL). The mixture was heated to reflux for 12 h. The hot mixture was filtered and the cake was washed with MeCN (6 mL). The filtrate was concentrated to half the volume and was diluted with EtOAc. The resulting solution was washed with water and brine, dried (MgSO$_4$), filtered and concentrated under reduced pressure. The residue was purified by flash chromatography (Hexane:EtOAc, 7:3) to provide the title compound (115 mg, 47% yield) as a yellow solid.

b) 11-Ethyl-5,11-dihydro-8-{2-[4-(5-formyl-2-furanyl)-2-methylphenoxy]ethyl}-5-methyl-6H-dipyrido[3,2-b:2',3'-e][1,4]diazepin-6-one DIAD (107 μL, 0.54 mmol) was added dropwise to a solution of 11-ethyl-5,11-dihydro-8-(2-hydroxyethyl)-5-methyl-6H-dipyrido[3,2-b:2',3'-e][1,4]diazepin-6-one (135 mg, 0.45 mmol), 5-(4-hydroxy-3-methylphenyl)-2-furanecarboxaldehyde (110 mg, 0.54 mmol) and PPh$_3$ (143 mg, 0.54 mmol) in THF (4 mL) at 25° C. The reaction mixture was stirred at 25° C. for 18 h. The mixture was concentrated under reduced pressure. The residue was purified by flash chromatography (Hexane:EtOAc, 3:2) to give the title compound (147 mg, 67% yield) as a pale yellow foam.

c) 5-{4-[2-(11-Ethyl-6,11-dihydro-5-methyl-6-oxo-5H-dipyrido[3,2-b:2',3'-e][1,4]diazepin-8-yl)ethoxy]-3-methylphenyl}-2-furanecarboxylic acid A solution of NaClO$_2$ (13.7 mg, 0.15 mmol) in water (0.5 mL) was added over 10 min to an ice-cold solution of 11-ethyl-5,11-dihydro-8-{2-[4-(5-formyl-2-furanyl)-2-methylphenoxy]ethyl}-5-methyl-6H-dipyrido[3,2-b:2',3'-e][1,4]diazepin-6-one (57.0 mg, 0.12 mmol), sulfamic acid (16.7 mg, 0.17 mmol) and aqueous NaH$_2$PO$_4$ solution (63.2 mg, 0.46 mmol in 0.5 mL water) in 1,4-dioxane (2 mL). The mixture was stirred at 0° C. for 15 min then Na$_2$SO$_3$ (17.3 mg, 0.14 mmol) was added. After 15 min, the reaction mixture was rendered acidic (pH 4) with aqueous 1 N HCl solution and extracted with CH$_2$Cl$_2$ (50 mL). The organic layer was washed with water (15 mL) and brine (15 mL), dried (MgSO$_4$), filtered and concentrated under reduced pressure. The residue was purified by reverse phase HPLC (CombiPrep ODS-AQ 50×20 mm, 5μ, 120 A, MeCN/water+ 0.10% TFA) to give the title compound 1046 (34 mg). The acid was treated with aqueous 1 N NaOH solution (67 μL, 1 equiv.) in water (15 mL) and MeCN (10 mL) and the resulting solution was frozen and lyophilized to give the sodium salt of the title compound 1046 (33 mg, 53% yield) as a white solid.

Example 5 (Entry 1047)

5-{4-[2-(11-Ethyl-6,11-dihydro-5-methyl-6-oxo-5H-dipyrido[3,2-b:2',3'-e][1,4]diazepin-8-yl)ethoxy] phenyl}-2-methyl-3-furanecarboxylic acid a) Ethyl 5-(4-aminophenyl)-2-methyl-3-furanecarboxylate A mixture of ethyl 2-methyl-5-(4-nitrophenyl)-3-furanecarboxylate (500 mg, 1.82 mmol), iron powder (325 mesh, 811 mg, 14.5 mmol) and aqueous 1 N HCl solution (0.36 mL, 0.36 mmol) in EtOH (5 mL) was heated to reflux for 2 h. The reaction mixture was filtered and concentrated under reduced pressure to give the title compound (396 mg, 89% yield) as a brown oil.

b) Ethyl 5-(4-hydroxyphenyl)-2-methyl-3-furanecarboxylate

A solution of $NaNO_2$ (111 mg, 1.61 mmol) in water (1 mL) was added over 5 min to an ice-cold suspension of ethyl 5-(4-aminophenyl)-2-methyl-3-furanecarboxylate (395 mg, 1.61 mmol) in aqueous 1 M $H_2SO_4$ solution (12 mL). The reaction mixture was stirred at 0° C. for 20 min then was heated to 90° C. for 1 h. The cooled mixture was extracted with EtOAc. The organic layer was washed with water (2×) and brine, dried ($MgSO_4$), filtered and concentrated under reduced pressure to yield the title compound (78 mg, 20% yield) as a white solid.

c) Ethyl 5-{4-[2-(11-ethyl-6,11-dihydro-5-methyl-6-oxo-5H-dipyrido[3,2-b:2',3'-e][1,4]diazepin-8-yl)ethoxy]phenyl}-2-methyl-3-furanecarboxylate DIAD (60 μL, 0.31 mmol) was added dropwise to a solution of 11-ethyl-5,11-dihydro-8-(2-hydroxyethyl)-5-methyl-6H-dipyrido[3,2-b:2',3'-e][1,4]diazepin-6-one (75.8 mg, 0.25 mmol), ethyl 5-(4-hydroxyphenyl)-2-methyl-3-furanecarboxylate (75 mg, 0.30 mmol) and $PPh_3$ (80.0 mg, 0.30 mmol) in THF (3 mL) at 25° C. The reaction mixture was stirred at 25° C. for 48 h. The mixture was concentrated under reduced pressure. The residue was purified by flash chromatography (Hexane:EtOAc, 3:2) to give the title compound (64 mg, 48% yield) as yellow oil.

d) 5-{4-[2-(11-Ethyl-6,11-dihydro-5-methyl-6-oxo-5H-dipyrido[3,2-b:2',3'-e][1,4]diazepin-8-yl)ethoxy]phenyl}-2-methyl-3-furanecarboxylic acid A mixture of ethyl 5-{4-[2-(11-ethyl-6,11-dihydro-5-methyl-6-oxo-5H-dipyrido[3,2-b:2',3'-e][1,4]diazepin-8-yl)ethoxy]phenyl}-2-methyl-3-furanecarboxylate (64.0 mg, 0.12 mmol) and aqueous 1 N NaOH solution (2.00 mL, 2.00 mmol) in MeOH (2 mL) and THF (2 mL) was stirred at 25° C. for 3 h. The reaction mixture was concentrated under reduced pressure. The residue was diluted with water and the resulting solution was washed with $Et_2O$ (3×). The aqueous layer was acidified with aqueous 1 N HCl solution (pH 3) and extracted with EtOAc. The organic layer was washed with water and brine, dried ($MgSO_4$), filtered and concentrated under reduced pressure. The title compound (53 mg, 0.11 mmol) was suspended in water (5 mL) and treated with aqueous 0.1 N NaOH solution (1.06 mL, 0.11 mmol). The mixture was diluted with MeCN (2 mL) and the resulting solution was frozen and lyophilized to give the corresponding sodium salt of the title compound 1047 (50 mg, 79% yield) as a pale yellow solid.

Example 6 (Entry 1076)

11-Ethyl-5,11-dihydro-5-methyl-8-{2-[2-methyl-4-(4-methyl-3-pyridinyl)phenoxy]ethyl}-6H-dipyrido[3,2-b:2',3'-e][1,4]diazepin-6-one A mixture of 2-{4-[2-(ethyl-6,11-dihydro-5-methyl-6-oxo-5H-dipyrido[3,2-b:2',3'-e]diazepin-8-yl)ethoxy]-3-methylphenyl}-4,4,5,5-tetramethyl-1,3,2-dioxoborolane (200 mg, 0.39 mmol), 3-bromo-4-methylpyridine (86.9 mg, 0.51 mmol) and $K_3PO_4$ (248 mg, 1.17 mmol) in 1,4-dioxane (8.0 mL) was degassed with $N_2$ for 45 min. $PdCl_2$(dppf) (1:1 complex with $CH_2Cl_2$, 28.4 mg, 38.9 μmol) and dppf (21.6 mg, 38.9 μmol) were next added and the reaction mixture was stirred under $N_2$ in a pressure tube at 100° C. for 16 h. The cooled mixture diluted with EtOAc (25 mL) was filtered. The filtrate was concentrated under reduced pressure. The residue was purified by flash chromatography (EtOAc:Hexane, 4:1 to EtOAc) to give the title compound 1076 (154 mg, 82% yield) as a white solid.

Example 7 (Entry 1077)

11-Ethyl-5,11-dihydro-5-methyl-8-{2-[2-methyl-4-(4-methyl-1-oxido-3-pyridinyl)phenoxy]ethyl}-6H-dipyrido[3,2-b:2',3'-e][1,4]diazepin-6-one A solution of 5,11-dihydro-11-ethyl-5-methyl-8-{2-[2-methyl-4-(4-methyl-3-pyridinyl)phenoxy]ethyl}-6H-dipyrido[3,2-b:2',3'-e][1,4]diazepin-6-one (114 mg, 0.24 mmol) and MCPBA (62.6 mg, 0.31 mmol) in $CH_2Cl_2$ (10 mL) was stirred at room temperature for 2 h. The reaction mixture was diluted with EtOAc (50 mL) and the resulting solution was washed with aqueous 10% $Na_2S_2O_3$ solution (3×10 mL), aqueous $NaHCO_3$ solution (3×10 mL), water (10 mL) and brine (10 mL), then dried ($MgSO_4$), filtered and concentrated under reduced pressure. The residue was purified by flash chromatography to give the title compound 1077 (55 mg, 47% yield) as a white solid.

Example 8 (Entry 1090)

11-Ethyl-5,11-dihydro-5-methyl-8-{2-[4-(4-pyridinyl)phenoxy]ethyl}-6H-dipyrido[3,2-b:2',3'-e][1,4]diazepin-6-one a) 4-[4-(Phenylmethoxy)phenyl]pyridine $Pd(PPh_3)_4$ (10.0 mg, 0.01 mmol) was added to a degassed ($N_2$) mixture of 4-(phenylmethoxy)phenylboronic acid (230 mg, 1.01 mmol), 4-bromopyridine hydrobromide (194 mg, 1.00 mmol), aqueous 1 M $Na_2CO_3$ solution (4.0 mL) in MeCN (4 mL). The reaction mixture was heated to 85° C. for 5 h. The cooled suspension was filtered and the resulting solid was washed with aqueous MeCN. The filtrate was extracted with $CH_2Cl_2$. The organic layer was dried ($MgSO_4$), filtered and concentrated under reduced pressure. The residue was purified by flash chromatography (EtOAc) and combined with the solid obtained by filtration to give the title compound (247 mg, 94% yield) as a white solid.

b) 4-(4-Hydroxyphenyl)pyridine

A solution 4-[4-(phenylmethoxy)phenyl]pyridine (120 mg, 0.46 mmol), $Pd(OH)_2/C$ (20% w/w, 10 mg) and aqueous 1.0 M HCl solution (0.5 mL) in MeOH (20 mL) was stirred under a hydrogen atmosphere (50 psi) for 17 h at 25° C. The catalyst was removed by filtration, $Et_3N$ (0.1 mL) was added and the filtrate was concentrated under reduced pressure. The residue was treated with hot THF. The resulting suspension was filtered and the filtrate concentrated under reduced pressure to give the title compound (69 mg, 88% yield) as a beige solid.

c) 11-Ethyl-5,11-dihydro-5-methyl-8-{2-[4-(4-pyridinyl)phenoxy]ethyl}-6H-dipyrido[3,2-b:2',3'-e][1,4]diazepin-6-one A solution of DIAD (96.9 μL, 0.50 mmol) in THF (0.5 mL) was added dropwise to a solution of 11-ethyl-5,11-dihydro-8-(2-hydroxyethyl)-5-methyl-6H-dipyrido[3,2-b:2',3'-e][1,4]diazepin-6-one (100 mg, 0.33 mmol), 4-(4-hydroxyphenyl)pyridine (61.0 mg, 0.36 mmol) and $PPh_3$ (132 mg, 0.50 mmol) in THF (5.0 mL) at 25° C. The mixture was stirred at 25° C. for 16 h. The reaction mixture was concentrated under reduced pressure and the residue was purified by flash chromatography (EtOAc to EtOAc:THF, 4:1) to yield the title compound 1090 (70 mg, 46% yield).

Example 9 (Entry 1091)

11-Ethyl-5,11-dihydro-5-methyl-8-{2-[4-(1-oxido-4-pyridinyl)phenoxy]ethyl}-6H-dipyrido[3,2-b:2',3'-e][1,4]diazepin-6-one A solution of 11-ethyl-5,11-dihydro-5-methyl-8-{2-[4-(4-pyridinyl)phenoxy]ethyl}-6H-dipyrido[3,2-b:2',3'-e][1,4]diazepin-6-one (45.0 mg, 0.10 mmol) and MCPBA (37.0 mg, 0.18 mmol) in $CH_2Cl_2$ (7 mL) was stirred at 25° C. for 2 h. The mixture was concentrated under reduced pressure and the residue was purified by reverse phase HPLC (CombiPrep ADS-AQ 50×20 mm, 5µ, 120 A, MeCN+0.10% TFA/water+0.10% TFA) to give the title compound 1091 (25 mg, 54% yield) as a white solid.

Example 10 (Entry 1093)

8-{2-[4-(2-Amino-4-thiazolyl)-2-methylphenoxy] ethyl}-11-ethyl-5,11-dihydro-5-methyl-6H-dipyrido[3,2-b:2',3'-e][1,4]diazepin-6-one a) 4-(2-Amino-4-thiazolyl)-2-methylphenol Thiourea (79.8 mg, 1.05 mmol) was added to a solution of 2-bromo-1-(4-hydroxy-3-methylphenyl)ethanone (200 mg, 0.87 mmol) in 1,4-dioxane (15 mL). The reaction mixture was stirred at 25° C. for 24 h. The resulting suspension was filtered and the solid was washed with 1,4-dioxane and dried under reduced pressure. The solid was suspended in water (30 mL), pH 7 buffer solution (15 mL) was added and the mixture was extracted with EtOAc (3×50 mL). The combined organic layers were successively washed with water (20 mL) and brine (20 mL), dried ($MgSO_4$), filtered and concentrated under reduced pressure. The residue was purified by flash chromatography (Hexane:EtOAc, 1:1) to give the title compound (180 mg, 100% yield).

b) 8-{2-[4-(2-Amino-4-thiazolyl)-2-methylphenoxy]ethyl}-11-ethyl-5,11-dihydro-5-methyl-6H-dipyrido[3,2-b:2',3'-e][1,4]diazepin-6-one DEAD (192 mg, 1.10 mmol) was added dropwise to an ice-cold solution of 11-ethyl-5,11-dihydro-8-(2-hydroxyethyl)-5-methyl-6H-dipyrido[3,2-b:2',3'-e][1,4]diazepin-6-one (274 mg, 0.92 mmol), 4-(2-amino-4-thiazolyl)-2-methylphenol (190 mg, 0.92 mmol) and $PPh_3$ (289 mg, 1.10 mmol) in THF (10 mL). The reaction mixture was stirred at 25° C. for 2 h then was concentrated under reduced pressure. The residue was purified by purified by reverse phase HPLC (CombiPrep ADS-AQ 50×20 mm, 5µ, 120 A, MeCN+0.10% TFA/water+0.10% TFA) to give the trifluoroacetic acid salt of the title compound 1093 (119 mg, 27% yield) as a white solid.

Example 11 (Entry 1094)

11-Ethyl-5,11-dihydro-8-{2-[4-(1H-imidazol-4-yl)-2-methylphenoxy]ethyl}-5-methyl-6H-dipyrido[3,2-b:2',3'-e][1,4]diazepin-6-one a) 2-Methyl-4-[1-(triphenylmethyl)-1H-imidazol-4-yl]phenol A solution of 2-bromo-1-(4-hydroxy-3-methylphenyl)ethanone (400 mg, 1.75 mmol) in formamide (10 mL) was stirred at 190° C. for 5 h. The excess formamide was distilled under reduced pressure. The residue was taken in EtOAc (50 mL) and the resulting solution was successively washed with pH 7.0 buffer solution (10 mL), water (10 mL) and brine (10 mL) then was dried ($MgSO_4$), filtered and concentrated under reduced pressure. A solution of the residue, $Et_3N$ (0.88 g, 8.73 mmol) and triphenylmethyl chloride (584 mg, 2.10 mmol) in DMF (10 mL) was stirred at 60° C. for 3 h. The reaction mixture was cooled to 25° C., acidified with aqueous 1.0 N HCl solution and diluted with EtOAc (200 mL). The resulting mixture was successively washed with water (3×50 mL) and brine (50 mL), then dried ($MgSO_4$), filtered and concentrated under reduced pressure. The residue was purified by flash chromatography (Hexane:EtOAc, 1:1) to yield the title compound (514 mg, 71% yield).

b) 11-Ethyl-5,11-dihydro-8-{2-{2-methyl-4-[1-(triphenylmethyl)-1H-imidazol-4-yl]phenoxy}ethyl}-5-methyl-6H-dipyrido[3,2-b:2',3'-e][1,4]diazepin-6-one DEAD (90.7 µL, 0.58 mmol) was added dropwise to a solution of 11-ethyl-5,11-dihydro-8-(2-hydroxyethyl)-5-methyl-6H-dipyrido[3,2-b:2',3'-e][1,4]diazepin-6-one (143 mg, 0.48 mmol), 2-methyl-4-[1-(triphenylmethyl)-1H-imidazol-4-yl)]phenol (200 mg, 0.48 mmol) and $PPh_3$ (151 mg, 0.58 mmol) in THF (10 mL) at 25° C. After stirring for 2 h at 25° C., the mixture was concentrated under reduced pressure. The residue was purified by flash chromatography ($CH_2Cl_2$:MeOH, 95:5) to give the title compound (180 mg, 54% yield).

c) 11-Ethyl-5,11-dihydro-8-{2-[4-(1H-imidazol-4-yl)-2-methylphenoxy]ethyl}-5-methyl-6H-dipyrido[3,2-b:2',3'-e][1,4]diazepin-6-one A solution of 11-ethyl-5,11-dihydro-8-{2-{2-methyl-4-[1-(triphenylmethyl)-1H-imidazol-4-yl]phenoxy}ethyl}-5-methyl-6H-dipyrido[3,2-b:2',3'-e][1,4]diazepin-6-one (180 mg, 0.26 mmol) and trifluoroacetic acid (8.0 mL) in $CH_2Cl_2$ (8.0 mL) was stirred at 25° C. for 3 h. The reaction mixture was concentrated under reduced pressure. The residue was purified by reverse phase HPLC (CombiPrep ADS-AQ 50×20 mm, 5µ, 120 A, MeCN+0.10% TFA/water+0.10% TFA) to give the trifluoroacetic acid salt of the title compound 1094 (82 mg, 70% yield) as a white solid.

Example 12 (Entry 1095)

11-Ethyl-5,11-dihydro-5-methyl-8-{2-[2-methyl-4-(1-methyl-1H-imidazol-4-yl)phenoxy]ethyl}-6H-dipyrido[3,2-b:2',3'-e][1,4]diazepin-6-one A 60% dispersion in oil of NaH (10.5 mg, 0.26 mmol) was added to an ice-cold solution of compound 1094 (54.5 mg, 0.12 mmol) in THF (3.0 mL). After 30 min, MeI (37 mg, 0.26 mmol) was added and the mixture was stirred at 25° C. for 2 h. A few drops of AcOH were added to the reaction mixture. The mixture was concentrated under reduced pressure and was purified by reverse phase HPLC (CombiPrep ADS-AQ 50×20 mm, 5µ, 120 A, MeCN+0.10% TFA/water+ 0.10% TFA) to give the trifluoroacetic acid salt of the title compound 1095 (31 mg, 56% yield), which contains 31% of the 1-methyl-1H-imidazol-5-yl isomer.

Example 13 (Entry 1096)

11-Ethyl-5,11-dihydro-8-{2-[4-(1H-imidazol-2-yl)-2-methylphenoxy]ethyl}-5-methyl-6H-dipyrido[3,2-b:2',3'-e][1,4]diazepin-6-one a) 11-Ethyl-8-[2-(4-formyl-2-methylphenoxy)ethyl]-5,11-dihydro-5-methyl-6H-dipyrido[3,2-b:2',3'-e][1,4]diazepin-6-one A solution of DIAD (395 µL, 2.15 mmol) in THF (0.8 mL) was added dropwise to a solution of 11-ethyl-5,11-dihydro-8-(2-hydroxyethyl)-5-methyl-6H-dipyrido[3,2-b:2',3'-e][1,4]diazepin-6-one (430 mg, 1.44 mmol), 4-hydroxy-3-methylbenzaldehyde (200 mg, 1.47 mmol) and $PPh_3$ (564 mg, 2.15 mmol) in THF (15 mL) at 25° C. The mixture was stirred at 25° C. for 16 h. The reaction mixture was concentrated under reduced pressure and the residue was purified by flash chromatography (EtOAc:toluene, 1:3) to yield the title compound (385 mg, 64% yield).

b) 11-Ethyl-5,11-dihydro-8-{2-[4-(1H-imidazol-2-yl)-2-methylphenoxy]ethyl}-5-methyl-6H-dipyrido[3,2-b:2',3'-e][1,4]diazepin-6-one A solution of 11-ethyl-8-[2-(4-formyl-2-methylphenoxy)ethyl]-5,11-dihydro-5-methyl-6H-dipyrido[3,2-b:2',3'-e][1,4]diazepin-6-one (107 mg, 0.26 mmol), glyoxal (40% w/w, 0.20 mL, 1.25 mmol), aqueous 15 M $NH_4OH$ solution (3.0 mL) and NaOAc (84.0 mg, 1.02 mmol) in MeOH (6.0 mL) was stirred at 25° C. for 21 h. Aqueous 1.0 M $Na_2CO_3$ solution was added and the mixture was extracted with EtOAc (2×). The combined organic layers were dried ($Na_2SO_4$), filtered and concentrated under reduced pressure. The residue was purified by flash chromatography (EtOAc to EtOAc:THF, 7:3) to give the title compound 1096 (30 mg, 26% yield) as a pale yellow solid.

Example 14 (Entry 1097)

11-Ethyl-5,11-dihydro-5-methyl-8-{2-[2-methyl-4-(1-methyl-1H-imidazol-2-yl)phenoxy]ethyl}-6H-dipyrido[3,2-b:2',3'-e][1,4]diazepin-6-one A mixture of 11-ethyl-5,11-dihydro-8-{2-[4-(1H-imidazol-2-yl)-2-methylphenoxy]ethyl}-5-methyl-6H-dipyrido[3,2-b:2',3'-e][1,4]diazepin-6-one (20.0 mg, 0.04 mmol), aqueous 5 M NaOH solution (15 µL, 0.05 mmol) and MeI (10 µL, 0.16 mmol) in MeCN (2.0 mL) was stirred at 25° C. for 1 h. The mixture was concentrated under reduced pressure, poured into water and extracted with EtOAc (2×). The combined organic layers were dried ($Na_2SO_4$), filtered and concentrated under reduced pressure. The residue was purified by reverse phase HPLC (CombiPrep ADS-AQ 50×20 mm, 5µ, 120 A, MeCN+0.10% TFA/water+0.10% TFA) to give the trifluoroacetic acid salt of the title compound 1097 (6.0 mg, 30% yield) as a white solid.

Example 15 (Entry 1098)

11-Ethyl-5,11-dihydro-8-{2-[4-(1H-imidazol-1-yl)-2-methylphenoxy]ethyl}-5-methyl-6H-dipyrido[3,2-b:2',3'-e][1,4]diazepin-6-one a) 8-[2-(4-Bromo-2-methylphenoxy)ethyl]-11-ethyl -5,11-dihydro-5-methyl-6H-dipyrido[3,2-b:2',3'-e][1,4]diazepin-6-one A solution of DIAD (0.44 mL, 2.40 mmol) in THF (1.0 mL) was added dropwise to an ice-cold solution of 11-ethyl-5,11-dihydro-8-(2-hydroxyethyl)-5-methyl-6H-dipyrido[3,2-b:2',3'-e][1,4]diazepin-6-one (480 mg, 1.61 mmol), 4-bromo-2-methylphenol (318 mg, 1.70 mmol) and $PPh_3$ (629 mg, 2.40 mmol) in THF (20 mL) at 25° C. The mixture was stirred at 0° C. for 3 h. The reaction mixture was concentrated under reduced pressure and the residue was purified by flash chromatography (Hexane:EtOAc, 7:3) to yield the title compound (437 mg, 58% yield) as a white solid.

b) Ethyl-5,11-dihydro-8-{2-[4-(1H-imidazol-1-yl)-2-methylphenoxy]ethyl}-5-methyl-6H-dipyrido[3,2-b:2',3'-e][1,4]diazepin-6-one A solution of the 8-[2-(4-bromo-2-methylphenoxy)ethyl]-11-ethyl-5,11-dihydro-5-methyl-6H-dipyrido[3,2-b:2',3'-e][1,4]diazepin-6-one (30 mg, 0.06 mmol), imidazole (7.0 mg, 0.10 mmol), CuBr (2 mg, 0.014 mmol), and $CsCO_3$ (23 mg, 0.07 mmol) in nitrobenzene (0.8 mL) was degassed under vacuum and argon. The solution was heated to 180° C. at for 36 h. The mixture was diluted with $CH_2Cl_2$ and filtered. The resulting solution was washed with water, dried ($Na_2SO_4$), filtered and concentrated under reduced pressure. The residue was purified by flash chromatography (EtOAc to THF:EtOAc, 1:3) followed by reverse phase HPLC (CombiPrep ODS-AQ 50×20 mm, 5µ, 120 A, MeCN+0.10% TFA/water+0.10% TFA) to give the trifluoroacetic acid salt of the title compound 1098 (28 mg, 77% yield) as a yellow gum.

Example 16 (Entry 1099)

11-Ethyl-5,11-dihydro-5-methyl-8-{2-[2-methyl-4-(4-oxazolyl)phenoxy]ethyl}-6H-dipyrido[3,2-b:2',3'-e][1,4]diazepin-6-one a) 4-(4-Oxazolyl)-2-methylphenol A solution of 2-bromo-1-(4-hydroxy-3-methylphenyl)ethanone (200 mg, 0.87 mmol) in formamide (10 mL) was heated to 110° C. for 24 h. The excess formamide was removed by distillation under reduced pressure. The resulting residue was partitioned between a pH 7.0 buffer solution (10 mL) and EtOAc (50 mL). The organic layer was washed with water (10 mL) and brine (10 mL), dried ($MgSO_4$), filtered and concentrated under reduced pressure. The residue was purified by flash chromatography (Hexane:EtOAc, 1:1) to yield the title compound (51 mg, 33% yield).

b) 11-Ethyl-5,11-dihydro-5-methyl-8-{2-[2-methyl-4-(4-oxazolyl)phenoxy]ethyl}-6H-dipyrido[3,2-b:2',3'-e][1,4] diazepin-6-one DEAD (51.0 mg, 0.29 mmol) was added dropwise to a solution of 11-ethyl-5,11-dihydro-8-(2-hydroxyethyl)-5-methyl-6H-dipyrido[3,2-b:2',3'-e][1,4]diazepin-6-one (72.8 mg, 0.24 mmol), 4-(4-oxazolyl)-2-methylphenol (51.0 mg, 0.29 mmol) and $PPh_3$ (76.8 mg, 0.29 mmol) in THF (4 mL) at 25° C. After stirring for 2 h at 25° C., the mixture was concentrated under reduced pressure. The residue was purified by flash chromatography ($CH_2Cl_2$:acetone, 95:5) to give the title compound 1099 (23.3 mg, 21% yield) as a pale yellow solid.

Example 17 (Entry 2001)

3'-[2-(11-Ethyl-6,11-dihydro-5-methyl-6-oxo-5H-dipyrido[3,2-b:2',3'-e][1,4]diazepin-8-yl)ethoxy]-[1,1'-biphenyl]-4-carboxylic acid a) Methyl 3'-hydroxy-[1,1'-biphenyl]-4-carboxylate An aqueous 0.4 M $Na_2CO_3$ solution (21.7 mL) was added to a solution of 3-bromophenol (500 mg, 2.89 mmol) and 4-boronobenzoic acid (480 mg, 2.89 mmol) in MeCN (14.5 mL). The mixture was degassed with argon (10 min) then $Pd(PPh_3)_4$ (168 mg, 0.14 mmol) was added. The reaction mixture was heated to 90° C. for 12 h. The cooled mixture was acidified with aqueous 1 N HCl solution and extracted with EtOAc. The organic layer was washed with brine, dried ($MgSO_4$), filtered and concentrated under reduced pressure. A solution of the residue in $Et_2O$ (150 mL) was treated with excess ethereal $CH_2N_2$ solution (ca. 0.6 M) then was concentrated under reduced pressure. The residue was purified by flash chromatography (Hexane:EtOAc, 85:15) to give the title compound (375 mg, 57% yield) as a yellow solid.

b) Methyl 3'-[2-(11-ethyl-6,11-dihydro-5-methyl-6-oxo-5H-dipyrido[3,2-b:2',3'-e][1,4]diazepin-8-yl)ethoxy]-[1,1'-biphenyl]-4-carboxylate A solution of DEAD (84 µL, 0.54 mmol) in THF (0.5 mL) was added over 2 h to an ice-cold solution of 11-ethyl-5, 11-dihydro-8-(2-hydroxyethyl)-5-methyl-6H-dipyrido[3,2-b:2',3'-e][1,4]diazepin-6-one (100 mg, 0.34 mmol), methyl 3'-hydroxy-[1,1'-biphenyl]-4-carboxylate (123 mg, 0.54 mmol) and PPh₃ (141 mg, 0.54 mmol) in THF (3.4 mL). The reaction mixture was stirred at 25° C. for 12 h then concentrated under reduced pressure. The residue was purified by flash chromatography (toluene:EtOAc, 85:15) to give the title compound (74 mg, 43% yield) as white gummy solid.

c) 3'-[2-(11-Ethyl-6,11-dihydro-5-methyl-6-oxo-5H-dipyrido[3,2-b:2',3'-e][1,4]diazepin-8-yl)ethoxy]-[1,1'-biphenyl]-4-carboxylic acid An aqueous 1 N NaOH solution (3.0 mL, 3.00 mmol) was added to a solution of methyl 3'-[2-(11-ethyl-6,11-dihydro-5-methyl-6-oxo-5H-dipyrido[3,2-b:2',3'-e][1,4]diazepin-8-yl)ethoxy]-[1,1'-biphenyl]-4-carboxylate (74 mg, 0.15 mmol) in a 2:1 mixture of THF and MeOH (3.4 mL). The mixture was stirred at 25° C. for 2 h. The resulting solution was acidified with aqueous 1 N HCl solution and the mixture was extracted with EtOAc (3×). The combined organic layers were washed with brine, dried (MgSO₄), filtered and concentrated under reduced pressure to give the title compound 2001 (35 mg, 49% yield) as a white solid.

Example 18 (Entry 3001)

4-{{4-[2-(11-Ethyl-6,11-dihydro-5-methyl-6-oxo-5H-dipyrido[3,2-b:2',3'-e][1,4]diazepin-8-yl)ethoxy]-3-methylbenzoyl}amino}benzoic acid a) Methyl 4-hydroxy-3-methylbenzoate A solution of 4-hydroxy-3-methylbenzoic acid (5.13 g, 33.7 mmol) and aqueous 12 N HCl solution (1.0 mL) in MeOH (100 mL) was heated to reflux for 16 h. The cooled reaction mixture was concentrated under reduced pressure and the residue was taken in EtOAc. The resulting solution was washed with aqueous saturated NaHCO₃ solution and brine, dried (MgSO₄), filtered and concentrated under reduced pressure. The residue was triturated with Hexane:EtOAc (9:1) to give the title compound (4.70 g, 84% yield) as a beige solid.

b) Methyl 4-[2-(11-ethyl-6,11-dihydro-5-methyl-6-oxo-5H-dipyrido[3,2-b:2',3'-e][1,4]diazepin-8-yl)ethoxy]-3-methylbenzoate A solution of DIAD (250 µL, 1.27 mmol) in THF (1 mL) was added dropwise to a solution of 11-ethyl-5,11-dihydro-8-(2-hydroxyethyl)-5-methyl-6H-dipyrido[3,2-b:2',3'-e][1,4]diazepin-6-one (346 mg, 1.16 mmol), methyl 4-hydroxy-3-methylbenzoate (212 mg, 1.27 mmol) and PPh₃ (333 mg, 1.27 mmol) in THF (5 mL) at 25° C. The reaction mixture was stirred at 25° C. for 1 h. The mixture was concentrated under reduced pressure. The residue was purified by flash chromatography (Hexane:EtOAc, 1:1) to give the title compound (471 mg, 91% yield) as white solid.

c) 4-[2-(11-Ethyl-6,11-dihydro-5-methyl-6-oxo-5H-dipyrido[3,2-b:2',3'-e][1,4]diazepin-8-yl)ethoxy]-3-methylbenzoic acid A solution of methyl 4-[2-(11-ethyl-6,11-dihydro-5-methyl-6-oxo-5H-dipyrido[3,2-b:2',3'-e][1,4]diazepin-8-yl)ethoxy]-3-methylbenzoate (471 mg, 1.05 mmol) and aqueous 1 N NaOH solution (5.0 mL, 5.0 mmol) in MeOH (10 mL) and THF (5 mL) was heated to 50° C. for 5 h. Aqueous 1 N HCl solution (6 mL) was added to the cooled reaction mixture. The resulting suspension was filtered and the solid was washed with water and dried to give the title compound (382 mg, 83% yield) as a white solid.

d) 4-[2-(11-Ethyl-6,11-dihydro-5-methyl-6-oxo-5H-dipyrido[3,2-b:2',3'-e][1,4]diazepin-8-yl)ethoxy]-3-methylbenzoyl chloride (COCl)₂ (25 µL, 0.87 mmol) and DMF (10 µL) were added to a solution of 4-[2-(11-ethyl-6,11-dihydro-5-methyl-6-oxo-5H-dipyrido[3,2-b:2',3'-e][1,4]diazepin-8-yl)ethoxy]-3-methylbenzoic acid (52.8 mg, 0.12 mmol) in CH₂Cl₂ (5 mL). The reaction mixture was heated to reflux for 1 h. The cooled mixture was concentrated under reduced pressure to give the title compound (55 mg, 100% yield), which was used without further purification.

e) Methyl 4-{{4-[2-(1-ethyl-6,11-dihydro-5-methyl-6-oxo-5H-dipyrido[3,2-b:2',3'-e][1,4]diazepin-8-yl)ethoxy]-3-methylbenzoyl}amino}benzoate A solution of 4-[2-(11-ethyl-6,11-dihydro-5-methyl-6-oxo-5H-dipyrido[3,2-b:2',3'-e][1,4]diazepin-8-yl)ethoxy]-3-methylbenzoyl chloride (47.0 mg, 0.11 mmol), methyl 4-aminobenzoate (15.8 mg, 0.11 mmol) and Et₃N (15.3 µL, 0.11 mmol) in CH₂Cl₂ (4 mL) was stirred at 25° C. for 5 h. The reaction mixture was diluted with EtOAc and the resulting solution was successively washed with aqueous saturated NaHCO₃ solution and brine, dried (MgSO₄), filtered and concentrated under reduced pressure. The residue was purified by flash chromatography (Hexane:EtOAc, 1:1) to give the title compound (45 mg, 76% yield) as a white solid.

f) 4-{{4-[2-(11-Ethyl-6,11-dihydro-5-methyl-6-oxo-5H-dipyrido[3,2-b:2',3'-e][1,4]diazepin-8-yl)ethoxy]-3-methylbenzoyl}amino}benzoic acid A mixture of methyl 4-{{4-[2-(11-ethyl-6,11-dihydro-5-methyl-6-oxo-5H-dipyrido[3,2-b:2',3'-e][1,4]diazepin-8-yl)ethoxy]-3-methylbenzoyl}amino}benzoate (43.0 mg, 0.076 mmol) and aqueous 1 N NaOH solution (0.5 mL, 0.5 mmol) in MeCN (4 mL) and water (0.2 mL) was stirred at 25° C. for 48 h. The reaction mixture was concentrated under reduced pressure and the residual aqueous phase was acidified with aqueous 1 N HCl solution. The resulting suspension was filtered and the recovered solid dried to give the title compound 3001 (22 mg). The corresponding sodium salt was obtained by treatment with aqueous 1 N NaOH solution (18 mg, 42% yield) as a white solid.

Example 19 (Entry 3004)

4-[2-(11-Ethyl-6,11-dihydro-5-methyl-6-oxo-5H-dipyrido[3,2-b:2',3'-e][1,4]diazepin-8-yl)ethoxy]-3-methyl-N-(1-oxido-4-pyridinyl)benzamide a) 4-[2-(11-Ethyl-6,11-dihydro-5-methyl-6-oxo-5H-dipyrido[3,2-b:2',3'-e][1,4]diazepin-8-yl)ethoxy]-3-methyl-N-(4-pyridinyl)benzamide A solution of 4-[2-(11-ethyl-6,11-dihydro-5-methyl-6-oxo-5H-dipyrido[3,2-b:2',3'-e][1,4]diazepin-8-yl)ethoxy]-3-methylbenzoyl chloride (47.4 mg, 0.11 mmol), 4-aminopyridine (9.88 mg, 0.11 mmol) and Et₃N (15.3 µL, 0.11 mmol) in CH₂Cl₂ (4 mL) was stirred at 25° C. for 5 h. The reaction mixture was diluted with EtOAc and the resulting solution was successively washed with aqueous saturated NaHCO₃ solution and brine, dried (MgSO₄), filtered and concentrated under reduced pressure to give the title compound (58 mg, 100% yield) as a colorless oil.

b) 4-[2-(11-Ethyl-6,11-dihydro-5-methyl-6-oxo-5H-dipyrido[3,2-b:2',3'-e][1,4]diazepin-8-yl)ethoxy]-3-methyl-N-(1-oxido-4-pyridinyl)benzamide A solution of 4-[2-(11-ethyl-6,11-dihydro-5-methyl-6-oxo-5H-dipyrido[3,2-b:2',3'-e][1,4]diazepin-8-yl)ethoxy]-3-methyl-N-(4-pyridinyl)benzamide (52.0 mg, 0.10 mmol) and 80% MCPBA (35 mg, 0.16 mmol) in CH₂Cl₂ (4 mL) was stirred at 25° C. for 4 h. Aqueous saturated NaHCO₃ solution was added and the phases were separated. The organic layer was dried (MgSO₄), filtered and concentrated under reduced pressure. The residue was purified by reverse phase HPLC (CombiPrep ODS-AQ 50×20 mm, 5µ, 120 A) using a gradient of MeCN/water containing TFA (0.06%) to provide the title compound 3004 (19 mg, 36%) as a white solid.

Example 20 (Entry 3022)

4-{{4-[2-(11-Ethyl-6,11-dihydro-5-methyl-6-oxo-5H-dipyrido[3,2-b:2',3'-e][1,4]diazepin-8-yl)ethoxy]-3-methylphenyl}amino}benzoic acid a) 1,1-Dimethylethyl N-{4-[2-(11-ethyl-6,11-dihydro-5-methyl-6-oxo-5H-dipyrido[3,2-b:2',3'-e][1,4]diazepin-8-yl)ethoxy]-3-methylphenyl}carbamate A solution of DIAD (258 µL, 1.31 mmol) in THF (4 mL) was added over 2 h to a solution of 11-ethyl-5,11-dihydro-8-(2-hydroxyethyl)-5-methyl-6H-dipyrido[3,2-b:2',3'-e][1,4]diazepin-6-one (300 mg, 1.01 mmol), 1,1-dimethylethyl N-(4-hydroxy-3-methylphenyl)carbamate (225 mg, 1.01 mmol) and PPh₃ (343 mg, 1.31 mmol) in THF (12 mL) at 25° C. The reaction mixture was stirred at 25° C. for 1 h. The mixture was concentrated under reduced pressure. The residue was purified by flash chromatography (Hexane:EtOAc, 7:3 to 1:1) to give the title compound (230 mg, 45% yield) as white solid.

b) 11-Ethyl-5,11-dihydro-8-[2-(4-amino-2-methylphenoxy)ethyl]-5-methyl-6H-dipyrido[3,2-b:2',3'-e][1,4]diazepin-6-one A mixture of 1,1-dimethylethyl N-{4-[2-(11-ethyl-6,11-dihydro-5-methyl-6-oxo-5H-dipyrido[3,2-b:2',3'-e][1,4]diazepin-8-yl)ethoxy]-3-methylphenyl}carbamate (540 mg, 1.07 mmol) and 4 N HCl in 1,4-dioxane (5.0 mL, 20 mmol) was stirred at 25° C. for 2 h. The reaction mixture was concentrated under reduced pressure. The residue was taken in water (6 mL) and the resulting solution was washed with EtOAc. The aqueous layer was rendered basic (pH 9) with aqueous 2 N NaOH solution and the mixture was extracted with EtOAc. The organic layer was dried (MgSO₄), filtered and concentrated under reduced pressure to yield the title compound (398 mg, 92% yield) as a beige foam.

c) Ethyl 4-{{4-[2-(11-ethyl-6,11-dihydro-5-methyl-6-oxo-5H-dipyrido[3,2-b:2',3'-e][1,4]diazepin-8-yl)ethoxy]-3-methylphenyl}amino}benzoate A degassed mixture of 11-ethyl-5,11-dihydro-8-[2-(4-amino-2-methylphenoxy)ethyl]-5-methyl-6H-dipyrido[3,2-b:2',3'-e][1,4]diazepin-6-one (100 mg, 0.25 mmol), ethyl 4-bromobenzoate (61.0 µL, 0.37 mmol), t-BuONa (36.0 mg, 0.37 mmol), Pd₂(dba)₃ (2.5 mg, 2.7 µmol) and (+/−)-BINAP (5.0 mg, 8.0 1mol) in toluene (8 mL) was heated to 105° C. under nitrogen for 48 h. The cooled reaction mixture was diluted with EtOAc, filtered through a short pad of diatomaceous earth and was concentrated under reduced pressure. The residue was purified by flash chromatography (Hexane:EtOAc, 1:1) to give the title compound (55 mg, 40% yield) as a white solid.

d) 4-{{4-[2-(11-Ethyl-6,11-dihydro-5-methyl-6-oxo-5H-dipyrido[3,2-b:2',3'-e][1,4]diazepin-8-yl)ethoxy]-3-methylphenyl}amino}benzoic acid A solution of ethyl 4-{{4-[2-(11-ethyl-6,11-dihydro-5-methyl-6-oxo-5H-dipyrido[3,2-b:2',3'-e][1,4]diazepin-8-yl)ethoxy]-3-methylphenyl}amino}benzoate (55.0 mg, 0.10 mmol) and aqueous 1 N LiOH solution (1.0 mL, 1.0 mmol) in THF (3 mL) and MeOH (1 mL) was stirred at 25° C. for 18 h. The reaction mixture was rendered acidic (pH 6.5) with aqueous 1 N HCl solution and was extracted with EtOAc (2×). The combined organic layers were dried (MgSO₄), filtered and concentrated under reduced pressure. The residue was purified by reverse phase HPLC (CombiPrep ODS-AQ 50×20 mm, 5µ, 120 A) using a gradient of MeCN/water containing TFA (0.06%). The resulting solid (trifluoroacetic acid salt) was dissolved in EtOAc and the solution was extracted with aqueous 1.0 N HCl solution (2×). The pH of the combined aqueous layers was adjusted to 6.0–6.5 with aqueous 1 N NaOH solution and the resulting solution was extracted with EtOAc (2×). The combined organic layers were dried (MgSO₄), filtered and concentrated under reduced pressure. The residue (17 mg, 32 µmol) was suspended in MeCN (3 mL), aqueous 0.02 N NaOH solution (1.62 mL, 32 µmol) was added and the mixture was sonicated until a homogeneous solution was obtained. The solution was frozen and lyophilized to give the sodium salt of the title compound 3022 (15 mg, 29% yield) as a white solid.

Example 21 (Entry 4011)

4-[2-(11-Ethyl-6,11-dihydro-5-methyl-6-oxo-5H-dipyrido[3,2-b:2',3'-e][1,4]diazepin-8-yl)ethoxy]-3-methylbenzoic acid hydrazide A solution of methyl 4-[2-(11-ethyl-6,11-dihydro-5-methyl-6-oxo-5H-dipyrido[3,2-b:2',3'-e][1,4]diazepin-8-yl)ethoxy]-3-methylbenzoate (55.0 mg, 0.12 mmol) and hydrazine (130 µL, 4.14 mmol) in EtOH (10 mL) was heated to reflux for 16 h. The reaction mixture was concentrated under reduced pressure. The residue was purified by reverse phase HPLC (CombiPrep ODS-AQ 50×20 mm, 5µ, 120 A) using a gradient of MeCN/water containing TFA (0.06%) to provide the title compound 4011 (23 mg, 42%) as the trifluoroacetic acid salt.

Example 22 (Entry 4013)

4-[2-(11-Ethyl-6,11-dihydro-5-methyl-6-oxo-5H-dipyrido[3,2-b:2',3'-e][1,4]diazepin-8-yl)ethoxy]-3-methyl-N-(methylsulfonyl)benzamide A 1.0 M solution of DCC in CH₂Cl₂ (0.25 mL, 0.25 mmol) was added to a mixture of 4-[2-(11-ethyl-6,11-dihydro-5-methyl-6-oxo-5H-dipyrido[3,2-b:2',3'-e][1,4]diazepin-8-yl)ethoxy]-3-methylbenzoic acid (50.0 mg, 0.11 mmol), DMAP (24 mg, 0.19 mmol) and MeSO₂NH₂ (55 mg, 0.58 mmol) in THF (5 mL). After stirring at 25° C. for 72 h, the reaction mixture was acidified with aqueous 1 N HCl solution and extracted with EtOAc. The organic layer was washed with brine, dried (MgSO₄), filtered and concentrated under reduced pressure. The residue was purified by flash chromatography (EtOAc:Hexane, 50% to 100% containing 1% AcOH) to provide the title compound 4013 (25 mg, 42% yield).

TABLE 1

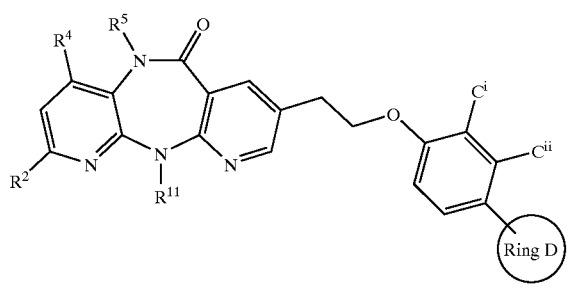
| Cpd entry # | R² | R⁴ | R⁵ | R¹¹ | C$^i$ | C$^{ii}$ | Ring D | m/z (MH)+ |
|---|---|---|---|---|---|---|---|---|
| 1001 | H | H | Me | Et | H | H | 4-(CO₂H)phenyl | 495 |
| 1002 | Cl | H | Me | Et | H | H | 4-(CO₂H)phenyl | 529 |
| 1003 | H | H | Me | Et | Me | H | 4-(CO₂H)phenyl | 509 |
| 1004 | H | H | Me | Et | F | H | 4-(CO₂H)phenyl | 513 |
| 1005 | H | H | Me | Et | H | Me | 4-(CO₂H)phenyl | 509 |
| 1006 | H | H | Me | Et | H | Cl | 4-(CO₂H)phenyl | 529 |
| 1007 | H | H | Me | Et | H | H | 4-(CH₂CO₂H)phenyl | 509 |

| | | | | | | | | |
|---|---|---|---|---|---|---|---|---|
| 1008 | H | H | Me | Et | Me | H | 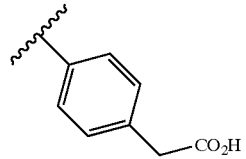 | 523 |
| 1009 | H | Me | H | Et | Me | H | 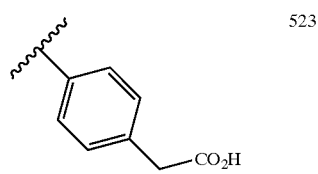 | 523 |
| 1010 | H | H | Me | Et | Me | H | 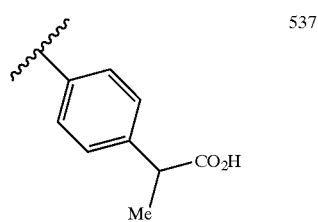 | 537 |
| 1011 | H | H | Me | Et | Me | H | 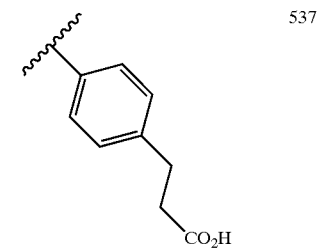 | 537 |
| 1012 | H | H | Me | Et | H | H | 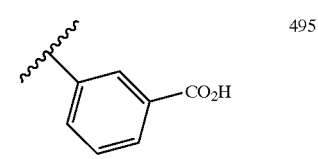 | 495 |
| 1013 | H | H | Me | Et | Me | H | 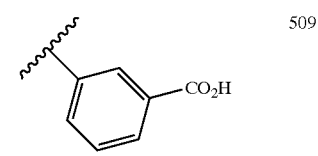 | 509 |
| 1014 | H | H | Me | Et | H | H | 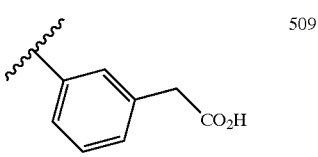 | 509 |
| 1015 | H | H | Me | Et | Me | H | 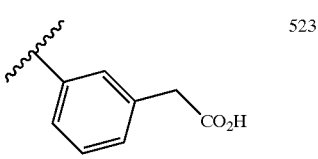 | 523 |
| 1016 | H | H | Me | Et | Me | H | 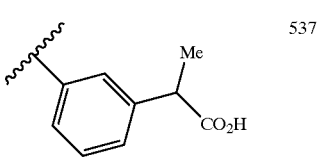 | 537 |

| | | | | | | | |
|---|---|---|---|---|---|---|---|
| 1017 | H | H | Me | Et | Me | H | 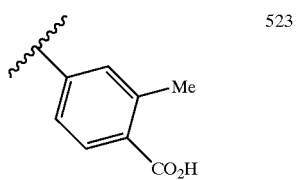 | 523 |
| 1018 | H | H | Me | Et | Me | H | 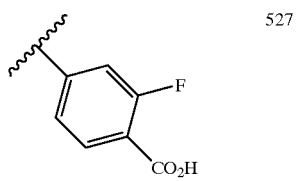 | 527 |
| 1019 | H | H | Me | Et | Me | H | 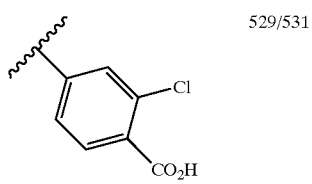 | 529/531 |
| 1020 | H | H | Me | Et | Me | H | 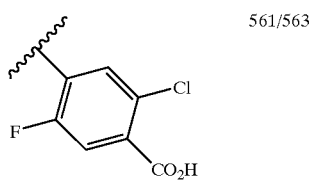 | 561/563 |
| 1021 | H | H | Me | Et | Me | H | 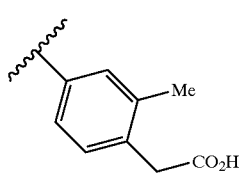 | 537 |
| 1022 | H | H | Me | Et | Me | H | 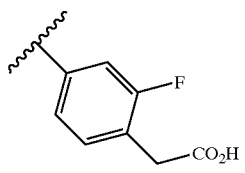 | 541 |
| 1023 | H | H | Me | Et | Me | H | 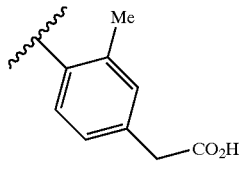 | 537 |
| 1024 | H | H | Me | Et | Me | H | 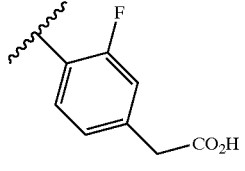 | 541 |
| 1025 | H | H | Me | Et | Me | H | 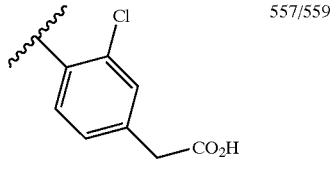 | 557/559 |

| | | | | | | | |
|---|---|---|---|---|---|---|---|
| 1026 | H | H | Me | Et | Me | H | 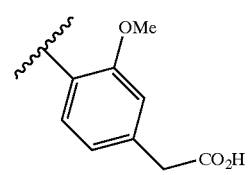 | 553 |
| 1027 | H | H | Me | Et | Me | H | 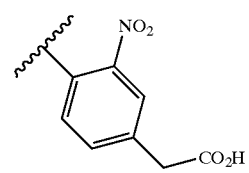 | 568 |
| 1028 | H | H | Me | Et | Me | H | 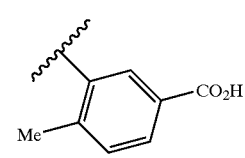 | 523 |
| 1029 | H | H | Me | Et | Me | H | 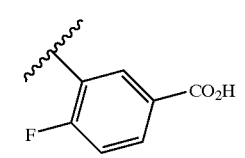 | 527 |
| 1030 | H | H | Me | Et | Me | H | 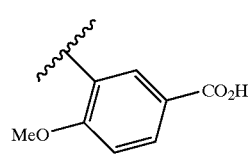 | 539 |
| 1031 | H | H | Me | Et | H | H | 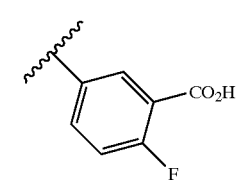 | 513 |
| 1032 | H | H | Me | Et | Me | H | 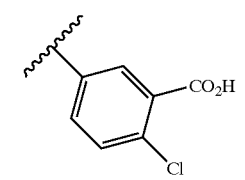 | 543/545 |
| 1033 | H | H | Me | Et | Me | H | 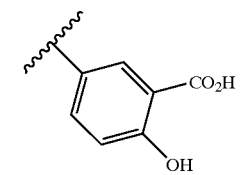 | 525 |
| 1034 | H | H | Me | Et | Me | H | 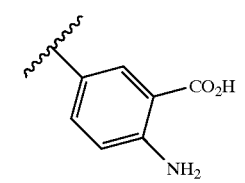 | 524 |

| | | | | | | | | |
|---|---|---|---|---|---|---|---|---|
| 1035 | H | H | H | Et | Me | H | 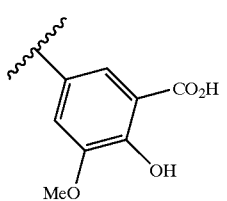 | 555 |
| 1036 | H | H | Me | Et | Me | H | 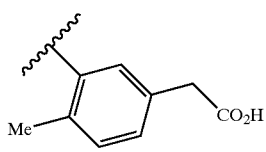 | 537 |
| 1037 | H | H | Me | Et | Me | H | 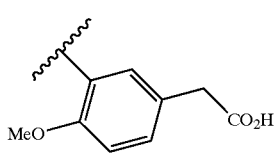 | 553 |
| 1038 | H | H | Me | Et | Me | H | 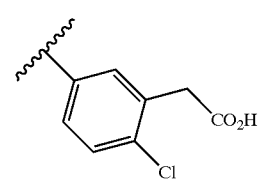 | 557/559 |
| 1039 | H | H | Me | Et | H | H | 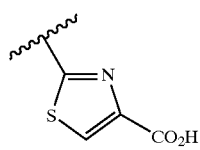 | 502 |
| 1040 | H | H | Me | Et | H | H | 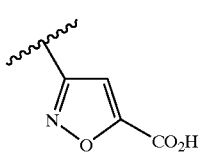 | 486 |
| 1041 | H | H | Me | Et | Me | H | 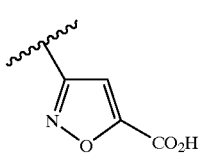 | 500 |
| 1042 | H | H | Me | Et | H | H | 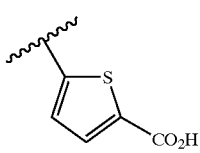 | 501 |
| 1043 | H | H | Me | Et | Me | H | 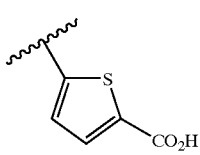 | 515 |
| 1044 | H | H | Me | Et | Me | H | 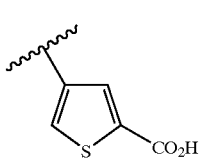 | 515 |

| | | | | | | | |
|---|---|---|---|---|---|---|---|
| 1045 | H | H | Me | Et | H | H | 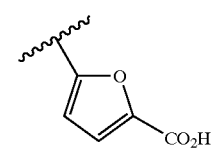 | 485 |
| 1046 | H | H | Me | Et | Me | H | 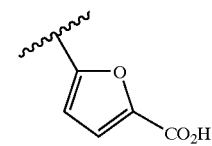 | 499 |
| 1047 | H | H | Me | Et | H | H | 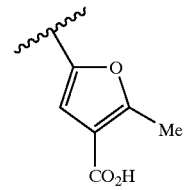 | 499 |
| 1048 | H | H | Me | Et | H | H | 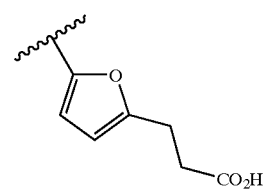 | 513 |
| 1049 | H | H | Me | Et | Me | H | 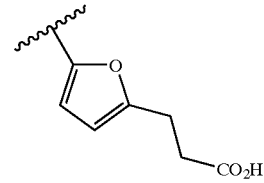 | 527 |
| 1050 | H | H | Me | Et | H | H | 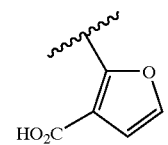 | 485 |
| 1051 | H | H | Me | Et | H | H | 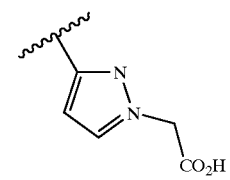 | 499 |
| 1052 | H | H | Me | Et | Me | H | 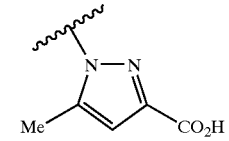 | 513 |
| 1053 | H | H | Me | Et | Me | H | 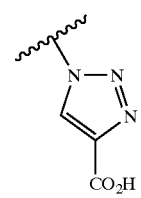 | 500 |

| | | | | | | | | |
|---|---|---|---|---|---|---|---|---|
| 1054 | H | H | Me | Et | Me | H | 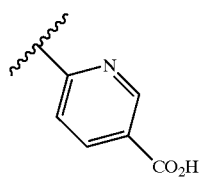 | 510 |
| 1055 | H | H | Me | Et | Me | H | 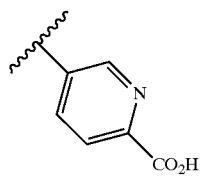 | 510 |
| 1056 | H | H | Me | Et | Me | H | 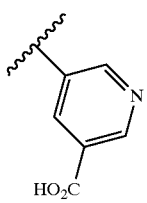 | 510 |
| 1057 | H | H | Me | Et | Me | H | 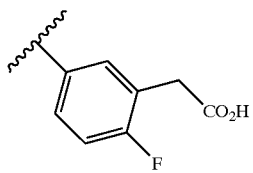 | 541 |
| 1058 | H | H | H | Et | Me | H | 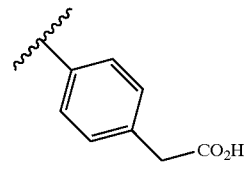 | 509 |
| 1059 | H | H | Me | H | Me | H | 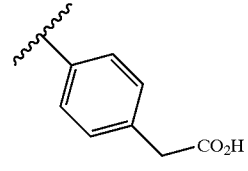 | 495 |
| 1060 | H | H | Me | Et | Me | H | 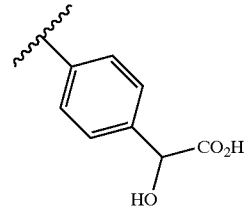 | 539 |
| 1061 | H | H | Me | Et | H | H | 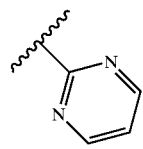 | 453 |
| 1062 | H | H | Me | Et | H | H | 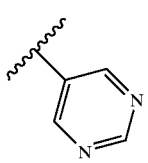 | 453 |

| | | | | | | | | |
|---|---|---|---|---|---|---|---|---|
| 1063 | H | H | Me | Et | Me | H | 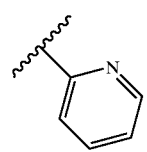 | 466 |
| 1064 | H | H | Me | Et | Me | H | 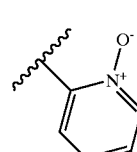 | 482 |
| 1065 | H | H | Me | Et | Me | H | 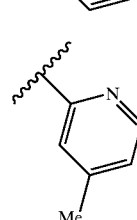 | 480 |
| 1066 | H | H | Me | Et | Me | H | 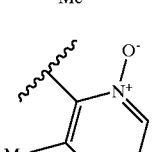 | 496 |
| 1067 | H | H | Me | Et | Me | H | 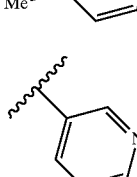 | 466 |
| 1068 | H | H | Me | Et | Me | H | 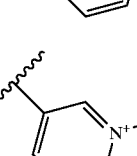 | 482 |
| 1069 | H | H | Me | 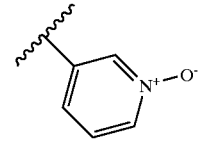 | Me | H | 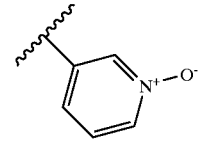 | 494 |
| 1070 | H | Me | H | Et | Me | H | 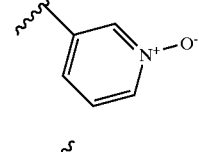 | 482 |
| 1071 | H | Me | H | 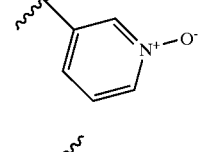 | Me | H | 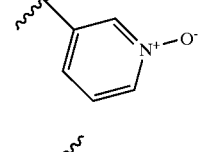 | 494 |
| 1072 | H | H | Me | Et | Me | H | 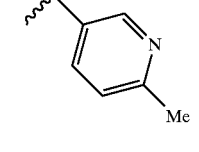 | 480 |

| | | | | | | | | |
|---|---|---|---|---|---|---|---|---|
| 1073 | H | H | Me | Et | Me | H | 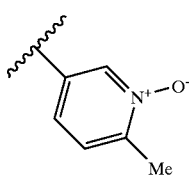 | 496 |
| 1074 | H | H | Me | Et | Me | H | 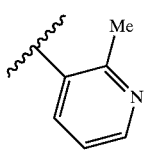 | 480 |
| 1075 | H | H | Me | Et | Me | H | 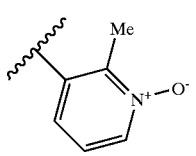 | 496 |
| 1076 | H | H | Me | Et | Me | H | 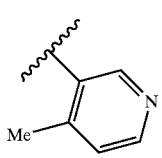 | 480 |
| 1077 | H | H | Me | Et | Me | H | 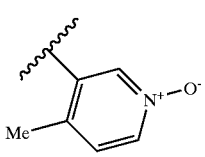 | 496 |
| 1078 | H | H | Me | Et | Me | H | 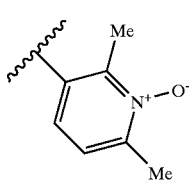 | 510 |
| 1079 | H | H | Me | Et | Me | H | 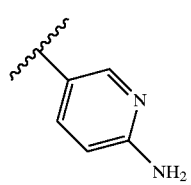 | 481 |
| 1080 | H | H | Me | Et | Me | H | 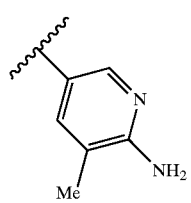 | 495 |
| 1081 | H | H | Me | Et | Me | H | 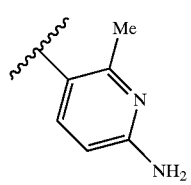 | 495 |

| | | | | | | | |
|---|---|---|---|---|---|---|---|
| 1082 | H | H | Me | Et | Me | H | 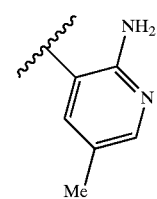 | 495 |
| 1083 | H | H | Me | Et | Me | H | 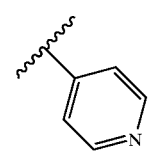 | 466 |
| 1084 | H | H | Me | Et | Me | H | 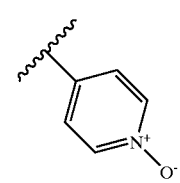 | 482 |
| 1085 | H | H | Me | Et | Me | H | 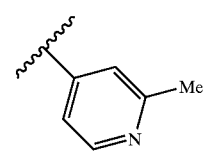 | 480 |
| 1086 | H | H | Me | Et | Me | H | 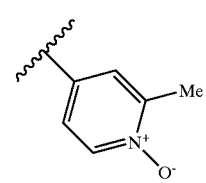 | 496 |
| 1087 | H | H | Me | Et | Me | H | 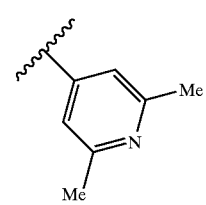 | 494 |
| 1088 | H | H | Me | Et | Me | H | 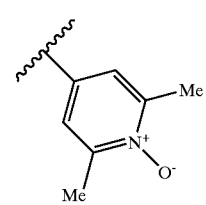 | 510 |
| 1089 | H | H | Me | Et | Me | H | 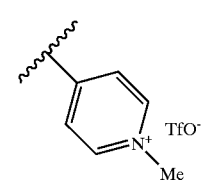 | 480 |
| 1090 | H | H | Me | Et | H | H | 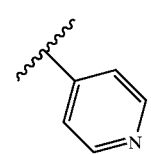 | 452 |

| | | | | | | | |
|---|---|---|---|---|---|---|---|
| 1091 | H | H | Me | Et | H | H | 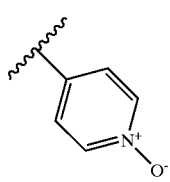 | 468 |
| 1092 | H | H | Me | Et | H | H | 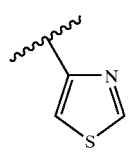 | 458 |
| 1093 | H | H | Me | Et | Me | H | 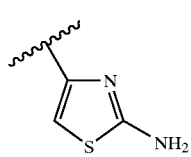 | 487 |
| 1094 | H | H | Me | Et | Me | H | 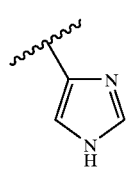 | 455 |
| 1095 | H | H | Me | Et | Me | H | 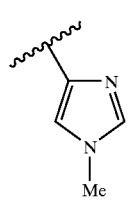 | 469 |
| 1096 | H | H | Me | Et | Me | H | 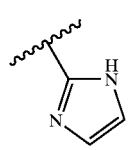 | 455 |
| 1097 | H | H | Me | Et | Me | H | 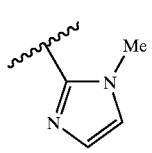 | 469 |
| 1098 | H | H | Me | Et | Me | H | 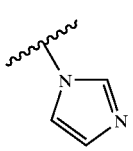 | 455 |
| 1099 | H | H | Me | Et | Me | H | 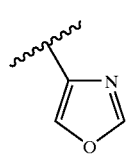 | 456 |
| 1100 | H | H | H | Et | Me | H | 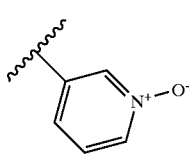 | 468 |

| | | | | | | | | |
|---|---|---|---|---|---|---|---|---|
| 1101 | H | H | Me | Et | H | H | 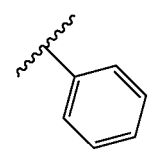 | 451 |
| 1102 | H | H | Me | Et | Me | H | 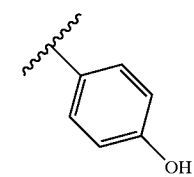 | 481 |
| 1103 | H | H | Me | Et | Me | H | 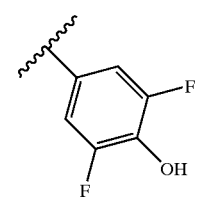 | 517 |
| 1104 | H | H | Me | Et | $CH_2OH$ | H | 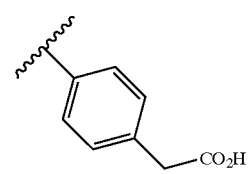 | 539 |
| 1105 | H | H | Me | Et | Me | H | 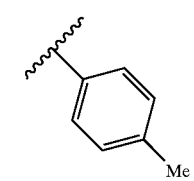 | 479 |
| 1106 | H | H | Me | Et | Me | H | 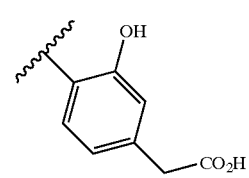 | 539 |
| 1107 | H | H | Me | Et | Me | H | 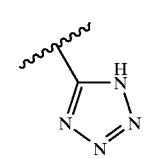 | 457 |
| 1108 | H | H | Me | Et | Me | H | 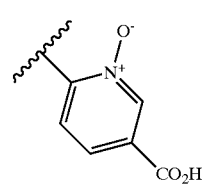 | 526 |
| 1109 | H | H | Me | Et | Me | H | 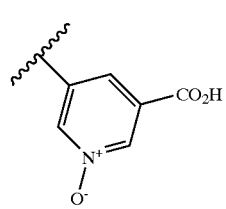 | 526 |

| 1110 | H | H | Me | Et | Me | H | 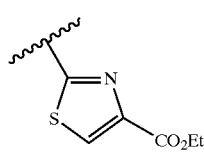 | 530 |
TABLE 2
| Cpd entry | R² | R⁴ | R⁵ | R¹¹ | Ring D | m/z (MH)+ |
|---|---|---|---|---|---|---|
| 2001 | H | H | Me | Et | 4-HO₂C-C₆H₄- | 495 |
| 2002 | H | H | Me | Et | 3-HO₂C-C₆H₄- | 495 |
| 2003 | H | H | Me | Et | C₆H₅- | 451 |
TABLE 3
| Cpd. entry # | R⁴ | R⁵ | E | Ring D | MS ES⁺ (MH) |
|---|---|---|---|---|---|
| 3001 | H | Me | CONH | 4-COOH-C₆H₄- | 552 |
| 3002 | H | Me | CONHCH₂ | 4-COOH-C₆H₄- | 566 |
| 3003 | H | Me | CONHCH₂ | 4-pyridyl N-oxide | 539 |
| 3004 | H | Me | CONH | 4-pyridyl N-oxide | 525 |
| 3005 | H | Me | CONH | 4-(CH₂COOH)-C₆H₄- | 566 |
| 3006 | H | Me | CONMeCH₂ | 4-COOH-C₆H₄- | 580 |

TABLE 3-continued
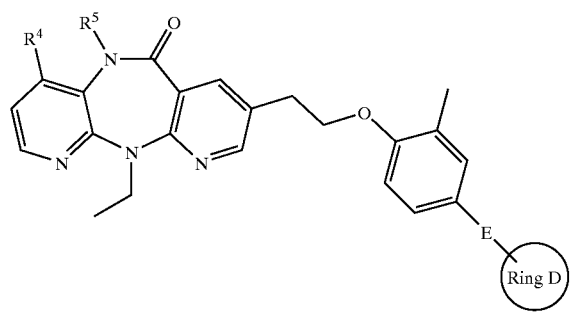
| Cpd. entry # | R⁴ | R⁵ | E | Ring D | MS ES⁺ (MH) |
|---|---|---|---|---|---|
| 3007 | H | Me | CONH | 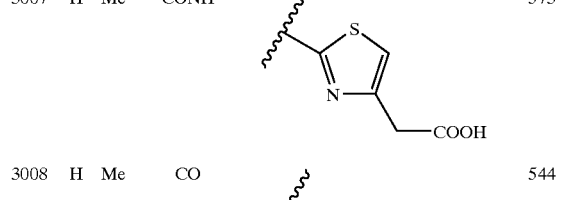 | 573 |
| 3008 | H | Me | CO | 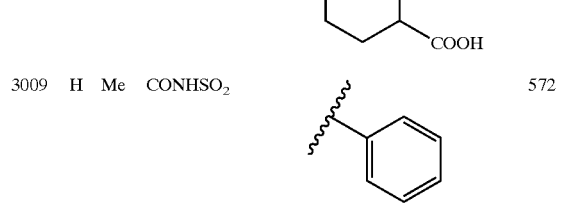 | 544 |
| 3009 | H | Me | CONHSO₂ | 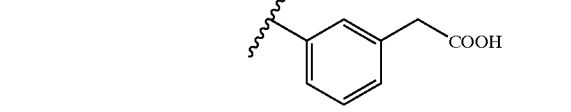 | 572 |
| 3010 | H | Me | CONH | 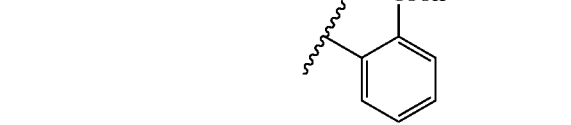 | 566 |
| 3011 | H | Me | CONH | 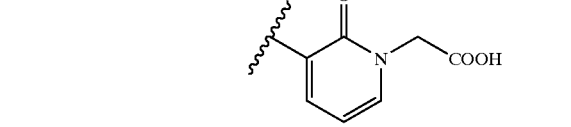 | 552 |
| 3012 | H | Me | CONH | 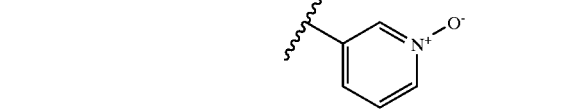 | 583 |
| 3013 | H | Me | CONH | 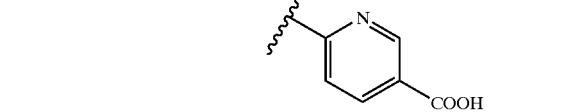 | 525 |
| 3014 | H | Me | CONH | 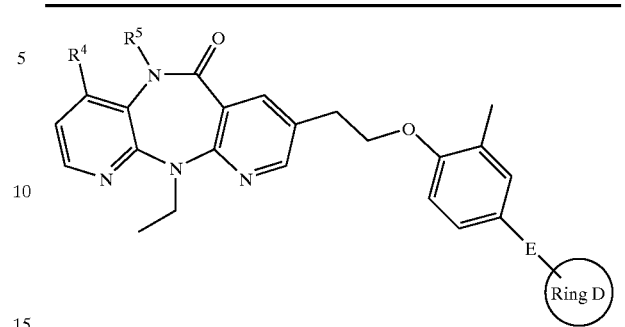 | 553 |
TABLE 3-continued
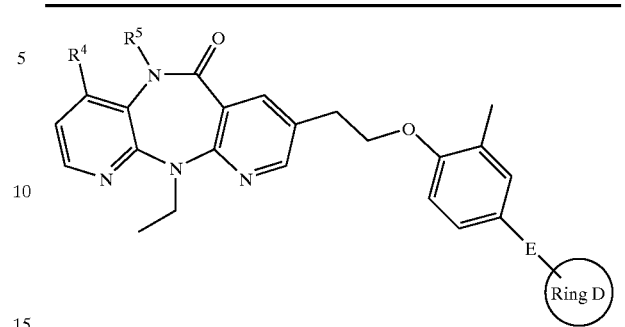
| Cpd. entry # | R⁴ | R⁵ | E | Ring D | MS ES⁺ (MH) |
|---|---|---|---|---|---|
| 3015 | H | Me | CONH | 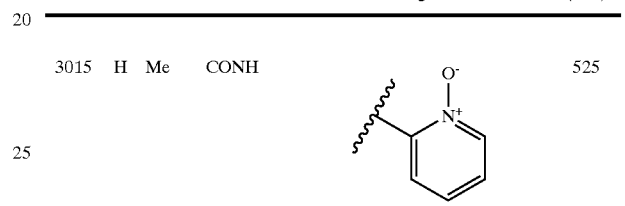 | 525 |
| 3016 | H | Me | CONMe | 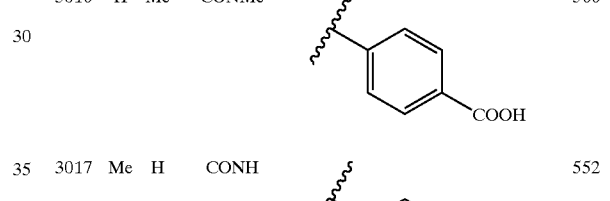 | 566 |
| 3017 | Me | H | CONH | 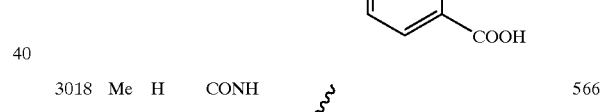 | 552 |
| 3018 | Me | H | CONH | 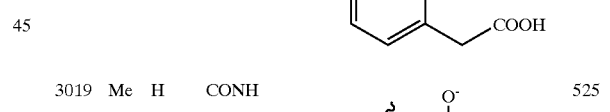 | 566 |
| 3019 | Me | H | CONH | 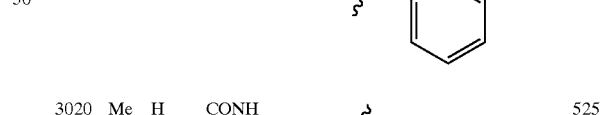 | 525 |
| 3020 | Me | H | CONH | 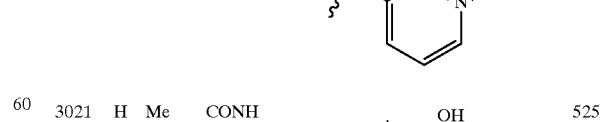 | 525 |
| 3021 | H | Me | CONH |  | 525 |

TABLE 3-continued
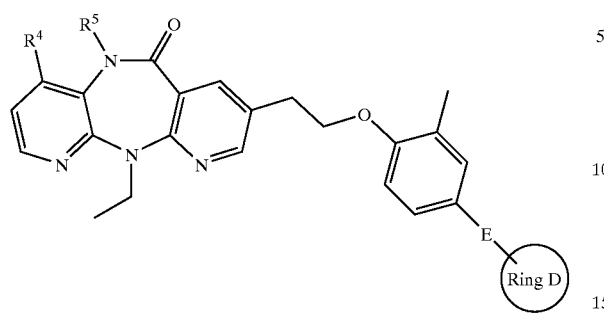
| Cpd. entry # | R⁴ | R⁵ | E | Ring D | MS ES⁺ (MH) |
|---|---|---|---|---|---|
| 3022 | H | Me | NH | 4-(HO₂C)C₆H₄– | 524 |
| 3023 | H | Me | NMe | 4-(HO₂C)C₆H₄– | 538 |
| 3024 | H | Me | NH | 3-(HO₂CCH₂)C₆H₄– | 538 |
| 3025 | H | Me | NH | 6-(HO₂C)pyridin-2-yl | 525 |
| 3026 | H | Me | NH | 4-(HO₂C)thiazol-2-yl | 531 |
TABLE 3-continued
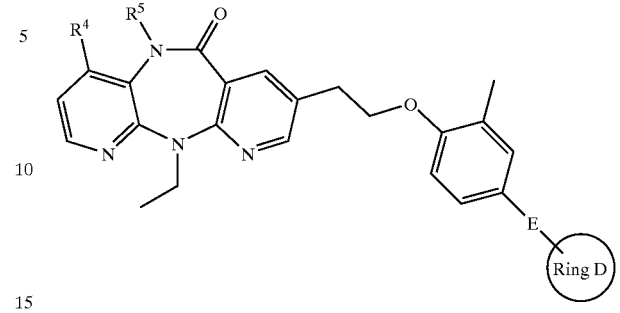
| Cpd. entry # | R⁴ | R⁵ | E | Ring D | MS ES⁺ (MH) |
|---|---|---|---|---|---|
| 3027 | H | Me | CO | 4-(HO₂C)C₆H₄– | 537 |
| 3028 | H | Me | SO₂ | 4-(HO₂C)C₆H₄– | 573 |
| 3029 | H | Me | SO₂ | 3-(HO₂CCH₂)C₆H₄– | 587 |
| 3030 | H | Me | SO₂NH | 4-(CO₂H)C₆H₄– | 588 |
| 3031 | H | Me | NHCONH | 4-(CO₂H)C₆H₄– | 567 |
| 3032 | H | Me | NHCO | 4-(CO₂H)C₆H₄– | 552 |

TABLE 3-continued

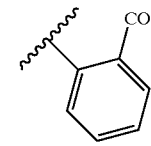

| Cpd. entry # | R⁴ | R⁵ | E | Ring D | MS ES⁺ (MH) |
|---|---|---|---|---|---|
| 3033 | H | Me | NHCO | 2-COOH-phenyl | 552 |
| 3034 | H | Me | NHCO | 6-(pyridin-3-yl)-5-CO₂H | 553 |
| 3035 | H | Me | NHCO | 6-chloro-pyridin-3-yl | 543/545 |
| 3036 | H | Me | NH | pyridin-2-yl | 481 |
| 3037 | H | Me | SO₂ | pyridin-4-yl | 530 |

TABLE 4

| Cpd. entry # | R⁴ | R⁵ | E | m/z (MH)+ |
|---|---|---|---|---|
| 4001 | H | Me | NHC(O)Me | 446 |

TABLE 4-continued

| Cpd. entry # | R⁴ | R⁵ | E | m/z (MH)+ |
|---|---|---|---|---|
| 4002 | H | Me | N(COMe)CH₂CO₂H | 504 |
| 4003 | H | Me | N(COMe)CH₂-(4-CO₂H-phenyl) | 580 |
| 4004 | H | Me | NHC(O)NHCH₂CO₂H | 505 |
| 4005 | H | Me | NHSO₂Me | 482 |
| 4006 | H | Me | NHC(O)CH₂CH₂CO₂H | 504 |
| 4007 | H | Me | NHC(O)CH₂-(1-CO₂H-cyclopentyl) | 558 |
| 4008 | H | Me | NHC(O)CH₂C(Me)₂CO₂H | 532 |
| 4009 | H | Me | NHC(O)-(1-CO₂H-cyclopropyl) | 516 |
| 4010 | H | Me | NHC(O)CH=CHCO₂H | 502 |
| 4011 | H | Me | CONHNH₂ | 447 |
| 4012 | H | Me | CONH—C(Me)₂—COOH | 518 |
| 4013 | H | Me | CONH—SO₂—Me | 510 |
| 4014 | H | Me | CONH—CH₂—C(Et)₂—COOH | 560 |
| 4015 | H | Me | CONH—NH—CH₂—COOH | 527 |

TABLE 4-continued

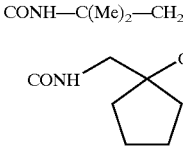

| Cpd. entry # | R⁴ | R⁵ | E | m/z (MH)+ |
|---|---|---|---|---|
| 4016 | H | Me | CONH—NH—Me | 461 |
| 4017 | H | Me | CONH—C(Me)₂—CH₂—COOH | 532 |
| 4018 | H | Me | CONH-CH₂-C(cyclopentyl)-COOH | 558 |
| 4019 | Me | H | CONH—NH₂ | 447 |
| 4020 | H | Me | SO₂NH—CH₂—COOH | 526 |

Reverse Transcriptase (RT) Assays

The assays are as described in WO 01/96338, the contents of which are herein incorporated by reference.

The results are listed in Table 5, as IC$_{50}$(nM) and EC$_{50}$ (nM).

Table Legend:

IC$_{50}$: A=>100 nM; B=100 nM–50 nM; C=<50 nM;
EC$_{50}$: A=>50 nM; B=50 nM–10 nM; C=<10 nM; and
NT=Not tested

TABLE 5

Inhibition of Wild type and mutant strains of RT for compounds of formula I

| Cpd entry# | IC$_{50}$ WT RT (nM) | IC$_{50}$ K103N/Y181C (nM) | EC$_{50}$ WT RT (nM) | EC$_{50}$ K103N/Y181C (nM) |
|---|---|---|---|---|
| 1001 | C | B | C | A |
| 1002 | C | C | C | NT |
| 1003 | C | C | C | C |
| 1004 | C | A | C | A |
| 1005 | C | A | B | A |
| 1006 | C | B | B | A |
| 1007 | C | B | B | A |
| 1008 | C | C | C | C |
| 1009 | C | C | B | B |
| 1010 | C | C | NT | B |
| 1011 | C | C | C | B |
| 1012 | C | A | C | B |
| 1013 | C | C | C | B |
| 1014 | C | A | C | B |
| 1015 | C | C | C | C |
| 1016 | C | B | NT | NT |
| 1017 | C | C | NT | NT |
| 1018 | C | C | NT | NT |
| 1019 | C | B | B | A |
| 1020 | C | C | NT | NT |
| 1021 | C | C | NT | B |
| 1022 | NT | C | C | C |
| 1023 | NT | B | NT | NT |
| 1024 | C | C | NT | B |
| 1025 | C | C | NT | NT |
| 1026 | C | C | NT | B |
| 1027 | C | B | NT | NT |
| 1028 | C | A | NT | B |
| 1029 | C | B | NT | NT |
| 1030 | C | A | NT | NT |
| 1031 | C | A | C | NT |
| 1032 | C | B | NT | B |
| 1033 | C | B | NT | A |
| 1034 | C | C | C | C |
| 1035 | C | C | NT | A |
| 1036 | C | B | NT | B |
| 1037 | C | B | NT | B |
| 1038 | C | C | NT | B |
| 1039 | C | A | NT | NT |
| 1040 | C | A | NT | NT |
| 1041 | C | C | A | A |
| 1042 | C | B | B | B |
| 1043 | C | C | C | B |
| 1044 | C | C | C | B |
| 1045 | C | B | NT | NT |
| 1046 | C | A | C | A |
| 1047 | C | A | B | A |
| 1048 | C | A | NT | NT |
| 1049 | C | A | NT | NT |
| 1050 | A | NT | NT | NT |
| 1051 | C | A | A | A |
| 1052 | C | A | B | A |
| 1053 | C | B | A | A |
| 1054 | C | C | NT | B |
| 1055 | NT | C | C | C |
| 1056 | NT | C | NT | NT |
| 1057 | C | C | NT | NT |
| 1058 | C | B | C | B |
| 1059 | C | A | C | A |
| 1060 | C | C | B | B |
| 1061 | C | A | NT | NT |
| 1062 | C | A | NT | NT |
| 1063 | NT | C | C | C |
| 1064 | NT | C | C | C |
| 1065 | C | C | NT | NT |
| 1066 | B | NT | NT | NT |
| 1067 | C | C | NT | C |
| 1068 | C | C | C | C |
| 1069 | C | A | C | B |
| 1070 | NT | C | NT | C |
| 1071 | NT | B | C | B |
| 1072 | NT | C | NT | C |
| 1073 | C | C | C | C |
| 1074 | C | C | NT | NT |
| 1075 | C | C | C | C |
| 1076 | C | C | NT | NT |
| 1077 | C | C | NT | NT |
| 1078 | C | C | NT | NT |
| 1079 | C | C | NT | NT |
| 1080 | C | C | NT | NT |
| 1081 | C | C | NT | NT |
| 1082 | C | C | NT | NT |
| 1083 | C | C | C | C |
| 1084 | C | C | NT | NT |
| 1085 | C | C | NT | NT |
| 1086 | C | C | NT | NT |
| 1087 | C | C | NT | NT |
| 1088 | C | C | NT | NT |
| 1089 | NT | C | NT | C |
| 1090 | C | B | C | B |
| 1091 | C | C | C | C |
| 1092 | C | A | NT | NT |
| 1093 | C | C | C | C |
| 1094 | C | C | C | C |
| 1095 | C | C | C | C |
| 1096 | C | C | NT | C |
| 1097 | C | B | NT | B |
| 1098 | NT | C | NT | C |

TABLE 5-continued

Inhibition of Wild type and mutant strains of RT for compounds of formula I

| Cpd entry# | IC$_{50}$ WT RT (nM) | IC$_{50}$ K103N/Y181C (nM) | EC$_{50}$ WT RT (nM) | EC$_{50}$ K103N/Y181C (nM) |
|---|---|---|---|---|
| 1099 | C | C | C | C |
| 1100 | C | NT | C | B |
| 1101 | C | B | C | A |
| 1102 | C | C | C | C |
| 1103 | C | B | NT | NT |
| 1104 | C | C | C | B |
| 1105 | C | C | NT | NT |
| 1106 | C | B | B | A |
| 1107 | C | A | NT | NT |
| 1108 | C | C | B | B |
| 1109 | C | C | A | A |
| 1110 | C | A | NT | NT |
| 2001 | A | NT | NT | NT |
| 2002 | A | NT | NT | NT |
| 2003 | C | A | NT | NT |
| 3001 | C | C | C | B |
| 3002 | C | C | NT | NT |
| 3003 | C | B | NT | NT |
| 3004 | C | C | C | C |
| 3005 | C | C | C | B |
| 3006 | C | B | NT | NT |
| 3007 | C | C | B | A |
| 3008 | C | B | B | NT |
| 3009 | C | A | B | A |
| 3010 | C | C | B | B |
| 3011 | C | A | B | A |
| 3012 | C | B | A | A |
| 3013 | C | C | NT | NT |
| 3014 | C | C | NT | B |
| 3015 | C | C | NT | NT |
| 3016 | C | B | NT | B |
| 3017 | C | C | B | A |
| 3018 | C | C | B | A |
| 3019 | C | B | C | C |
| 3020 | C | C | C | C |
| 3021 | C | C | C | C |
| 3022 | C | C | C | B |
| 3023 | C | B | NT | NT |
| 3024 | C | C | C | C |
| 3025 | NT | C | NT | B |
| 3026 | NT | B | C | B |
| 3027 | C | B | C | B |
| 3028 | C | C | NT | A |
| 3029 | NT | C | NT | A |
| 3030 | C | C | A | A |
| 3031 | C | C | B | A |
| 3032 | C | C | B | A |
| 3033 | C | A | C | B |
| 3034 | C | C | NT | A |
| 3035 | C | C | NT | NT |
| 3036 | NT | C | NT | C |
| 3037 | NT | C | NT | C |
| 4001 | C | B | NT | NT |
| 4002 | C | A | NT | NT |
| 4003 | B | A | NT | NT |
| 4004 | C | A | B | NT |
| 4005 | C | C | NT | NT |
| 4006 | C | B | B | A |
| 4007 | C | A | C | C |
| 4008 | C | A | C | B |
| 4009 | C | A | C | A |
| 4010 | C | B | A | NT |
| 4011 | C | C | C | C |
| 4012 | C | B | B | A |
| 4013 | C | A | B | A |
| 4014 | C | C | C | B |
| 4015 | C | A | B | NT |
| 4016 | C | C | C | C |
| 4017 | C | A | C | A |
| 4018 | C | A | C | B |
| 4019 | C | B | NT | NT |
| 4020 | C | C | A | A |

What is claimed is:

1. A compound represented by formula I:

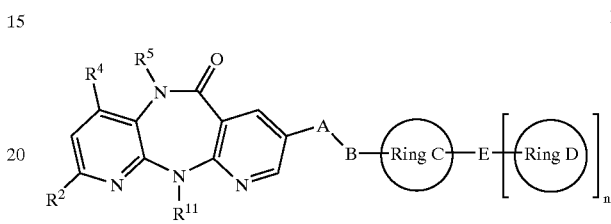

(I)

wherein $R^2$ is selected from: H, $(C_{1-4})$alkyl, halo, haloalkyl, OH, $(C_{1-6})$alkoxy, NH$(C_{1-4}$alkyl$)$ or N$(C_{1-4}$alkyl$)_2$;

$R^4$ is H or Me;

$R^5$ is H or Me;

$R^{11}$ is H, $(C_{1-4})$alkyl, $(C_{3-4})$cycloalkyl and $(C_{1-4})$alkyl-$(C_{3-4})$cycloalkyl;

A is a connecting chain of $(C_{1-3})$alkylene;

B is O or S;

n is 1;

wherein Ring C is a 6- or 10-membered aryl
said aryl being optionally substituted with from 1 to 4 substituents selected from:
halogen and $(C_{1-6})$alkyl optionally substituted with OH;

E is a single bond connecting group selected from:

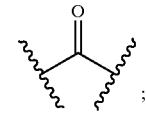

(vii)

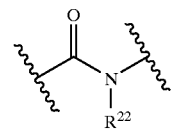

(viii)

wherein $R^{22}$ is H or $(C_{1-6})$alkyl;

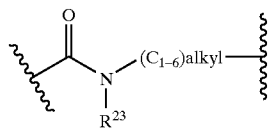

(ix)

wherein R²³ is H or (C₁₋₆)alkyl;

(x)

wherein R²⁴ is H or (C₁₋₆)alkyl;

(xi)

wherein R²⁵ is H or (C₁₋₆)alkyl;

(xii)

wherein R²⁶ $^{and\ R27}$ is each H or (C₁₋₆)alkyl;

(xiii)

wherein R²⁸ is H or (C₁₋₆)alkyl;

(xiv)

(xv)

wherein R²⁹ is H or (C₁₋₆)alkyl; and (xvi)

and

Ring D is a 6- or 10-membered aryl or a 5- or 6-membered heterocycle having from 1 to 4 heteroatoms selected from: O, N, and S, said aryl and said heterocycle being optionally substituted with from 1 to 5 substituents selected from:
halogen, NH₂, NO₂, COOH, OH, COO(C₁₋₆) alkyl, (C₁₋₆)alkoxy, (C₂₋₄)alkenyl-COOH, (C₃₋₇) cycloalkyl-COOH and (C₁₋₆)alkyl optionally substituted with COOH or OH;

or a salt or a prodrug thereof.

2. The compound according to claim 1, wherein:

R² is selected from: H, (C₁₋₄)alkyl, halo, haloalkyl, OH or (C₁₋₆)alkoxy;

E is a single bond or a connecting group selected from:

(vii)

(viii)

wherein R²² is H or (C₁₋₆)alkyl;

(ix)

wherein R²³ is H or (C₁₋₆)alkyl;

(x)

wherein R²⁴ is H or (C₁₋₆)alkyl;

(xi)

wherein R²⁵ is H or (C₁₋₆)alkyl;

(xii)

wherein $R^{26}$ and $R^{27}$ is each H or $(C_{1-6})$alkyl;

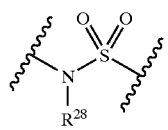
(xiii)

wherein $R^{28}$ is H or $(C_{1-6})$alkyl;

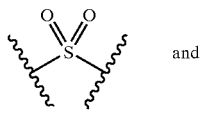
(xiv)

and

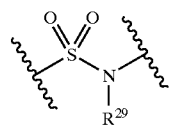
(xv)

wherein $R^{29}$ is H or $(C_{1-6})$alkyl;

and

Ring D is optionally substituted with: halogen, $NH_2$, $NO_2$, COOH, OH, $(C_{1-6})$alkoxy, $(C_{2-4})$alkenyl-COOH, $(C_{3-7})$cycloalkyl-COOH and $(C_{1-6})$alkyl optionally substituted with COOH or OH.

3. The compound of formula I according to claim 1, wherein A is —$CH_2$—$CH_2$—; B is O;

$R^2$ is H, Me, OMe, or halo; $R^4$ is H; $R^5$ is Me; $R^{11}$ is H, Et or $(C_{3-4})$ cycloalkyl;

Ring C is phenyl optionally substituted with from 1 or 2 substituents selected from: halogen and $(C_{1-6})$alkyl optionally substituted with OH;

Ring D is a phenyl or a 5- or 6-membered heterocycle having from 1 to 4 heteroatoms selected from: O, N, and S, said phenyl and said heterocycle being optionally substituted with from 1 to 4 substituents selected from:

halogen, $NH_2$, $NO_2$, COOH, OH, COO($C_{1-6}$alkyl), $(C_{1-6})$alkoxy, $(C_{1-6})$alkyl optionally substituted with COOH or OH; and $(C_{2-4})$alkenyl-COOH or $(C_{3-7})$ cycloalkyl-COOH;

or Ring D is thiophene, furan, thiazole, oxazole, isoxazole, pyrazole, triazole, imidazole, pyridine, pyridine-N-oxide, pyridinone, pyrimidine or tetrazole, each being optionally substituted with from 1 or 2 substituents selected from: halogen, $NH_2$, COOH, OH, $(C_{1-6})$alkoxy, $(C_{1-6})$alkyl optionally substituted with COOH or OH.

4. The compound according to claim 3, wherein $R^2$ is H, F or Cl; $R^{11}$ is Et or cyclopropyl;

Ring C is:

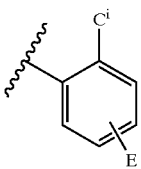 or 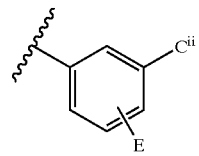

wherein $C^i$ is $(C_{1-6})$alkyl and $C^{ii}$ is H, halogen, or $(C_{1-6})$alkyl; and Ring D is selected from:
phenyl optionally substituted with 1 to 3 substituents selected from: COOH, OH, $(C_{1-6})$alkyl-COOH, or $(C_{1-6})$alkyl(OH)—COOH, $(C_{1-6})$alkyl, halogen, $(C_{1-6})$alkoxy, $NH_2$, and $NO_2$;

thiophene, furan or thiazole, each optionally substituted with from 1 to 3 substituents selected from: $NH_2$, COOH, and $(C_{1-6})$alkyl optionally substituted with COOH;

imidazole optionally substituted with from 1 or 2 $(C_{1-6})$alkyl substituents;

pyrazole optionally substituted with from 1 to 2 substituents selected from: COOH, $(C_{1-6})$alkyl optionally substituted with COOH;

triazole substituted with COOH;

isoxazole optionally substituted with COOH;

oxazole;

pyridine or pyridine-N-oxide, each optionally substituted with 1 to 3 substituents selected from: COOH, $(C_{1-6})$alkyl, halogen, $NH_2$, and OH;

pyrimidine;

pyridinone optionally substituted with 1 to 2 substituents selected from: $(C_{1-6})$alkyl optionally substituted with COOH; or tetrazole.

5. The compound according to claim 4, wherein $R^2$ is H; $R^{11}$ is Et; $C^i$ is $CH_3$ and $C^{ii}$ is H, Cl, or $CH_3$;

ring D is selected from:
phenyl optionally substituted with 1 or 2 substituents selected from: COOH, $CH_2COOH$, $CH_2CH_2COOH$, $CH_3$, F, Cl, OMe, $NO_2$, $NH_2$, and OH;

thiophene, furan or thiazole, each unsubstituted or mono- or di-substituted with COOH, —$CH_2$—COOH, or $NH_2$;

imidazole unsubstituted or mono-substituted with Me;

pyrazole unsubstituted or mono- or di-substituted with Me, COOH or —$CH_2$—COOH;

pyridine or pyridine-N-oxide, each mono- or di-substituted with Me, Cl, $NH_2$, or OH; and pyridinone mono-substituted on the nitrogen atom with —$CH_2$—COOH.

6. The compound according to claim 5, wherein Ring D is:

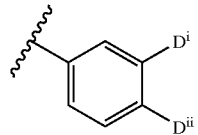

wherein $D^i$ is COOH, $(C_{1-6})$alkyl optionally substituted with COOH, or halogen, and $D^{ii}$ is COOH, OH, $NH_2$, halogen, $(C_{1-6})$alkyl optionally substituted with COOH, with the proviso that $D^i$ and $D^{ii}$ are not both COOH.

7. The compound according to claim 6, wherein $D^i$ is COOH, —$CH_2COOH$, Me, F, or Cl and $D^{ii}$ is OH, $NH_2$, F, Cl, —$CH_2COOH$ or COOH.

8. The compound according to claim 5, wherein ring D is phenyl mono-substituted with COOH, $CH_2COOH$, or $CH_2CH_2COOH$.

9. The compound according to claim 1, wherein n is 1 and E is a single bond or a connecting group selected from: —C(O)—; —C(O)—N($R^{22}$)— wherein $R^{22}$ is H or Me; —C(O)—N($R^{23}$)—($C_{1-6}$alkyl)- wherein $R^{23}$ is H or Me; —NH—C(O)—; —NH—C(O)—NH—; —$SO_2$—; —$SO_2$—NH— and —C(O)—NH—$SO_2$—.

10. The compound according to claim 9, wherein E is a connecting group selected from: —C(O)—N($R^{22}$)— wherein $R^{22}$ is H or Me; —N($R^{24}$)— wherein $R^{24}$ is H or Me; and NH—C(O)—.

11. The compound according to claim 10, wherein E is in the para position.

12. A pharmaceutical composition for the treatment of HIV infection, comprising a compound of formula I according to claim 1, or a pharmaceutically acceptable salt thereof, and a pharmaceutically acceptable carrier.

13. A method for the treatment of HIV infection, comprising administering to a patient an HIV inhibiting amount of a compound of formula I, according to claim 1, or a pharmaceutically acceptable salt thereof.

14. A method for the treatment of HIV infection, comprising administering to a patient an HIV inhibiting amount of a pharmaceutical composition according to claim 12.

15. A method for treating HIV infection comprising administering a compound of formula I, according to claim 1, or a pharmaceutically acceptable salt thereof, and a pharmaceutically acceptable carrier, in combination with an antiretroviral drug.

16. A method for preventing perinatal transmission of HIV-1 from mother to baby, comprising administering a compound of formula I, according to claim 1, or a pharmaceutically acceptable salt thereof, and a pharmaceutically acceptable carrier, to the mother before giving birth.

\* \* \* \* \*